United States Patent
Alfini et al.

(10) Patent No.: US 12,005,109 B2
(45) Date of Patent: Jun. 11, 2024

(54) MULTI-FUNCTIONALIZED NOMV CONJUGATES

(71) Applicant: GLAXOSMITHKLINE BIOLOGICALS SA, Rixensart (BE)

(72) Inventors: Renzo Alfini, Siena (IT); Roberta Di Benedetto, Siena (IT); Francesca Micoli, Siena (IT); Allan James Saul, Siena (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 74 days.

(21) Appl. No.: 16/636,560

(22) PCT Filed: Aug. 8, 2018

(86) PCT No.: PCT/EP2018/071482
§ 371 (c)(1),
(2) Date: Feb. 4, 2020

(87) PCT Pub. No.: WO2019/030271
PCT Pub. Date: Feb. 14, 2019

(65) Prior Publication Data
US 2022/0008529 A1 Jan. 13, 2022

(30) Foreign Application Priority Data
Aug. 10, 2017 (GB) .................................... 1712824

(51) Int. Cl.
| | | |
|---|---|---|
| A61K 39/095 | (2006.01) | |
| A61K 35/74 | (2015.01) | |
| A61K 39/00 | (2006.01) | |
| A61K 39/108 | (2006.01) | |
| A61K 47/69 | (2017.01) | |

(52) U.S. Cl.
CPC ............ *A61K 39/095* (2013.01); *A61K 35/74* (2013.01); *A61K 39/0258* (2013.01); *A61K 47/6911* (2017.08); *A61K 2039/6018* (2013.01); *A61K 2039/6087* (2013.01); *A61K 2039/627* (2013.01)

(58) Field of Classification Search
CPC .. A61K 39/095; A61K 35/74; A61K 39/0258; A61K 47/6911; A61K 2039/6018; A61K 2039/6087; A61K 2039/627; A61K 2039/55555; A61K 2039/6068;
(Continued)

(56) References Cited

FOREIGN PATENT DOCUMENTS

| WO | 1994008021 A1 | 4/1994 |
|---|---|---|
| WO | 2006/082530 A2 | 8/2006 |

(Continued)

OTHER PUBLICATIONS

Anonymous, "BS3 Protocol and Product Information Sheet Product." Jan. 1, 2014; p. 1; retrieved from the Internet: URL:http://www.proteochem.com/protocols/BS3-Product-Information-Sheet.pdf.

(Continued)

*Primary Examiner* — Gollamudi S Kishore

(57) ABSTRACT

The present invention is in the field of conjugating native, non-detergent extracted, outer membrane vesicles (nOMV) to multiple antigens to form multi functionalized nOMV-antigen conjugated derivatives, which are particularly useful for immunogenic compositions and immunisation; processes for the preparation and use of such conjugates are also provided.

14 Claims, 3 Drawing Sheets

Specification includes a Sequence Listing.

(58) Field of Classification Search
CPC .............. A61K 39/116; A61K 39/0275; A61K 39/385; Y02A 50/30; A61P 31/04
See application file for complete search history.

(56) References Cited

FOREIGN PATENT DOCUMENTS

| WO | 2014/053521 | * | 4/2014 |
| WO | 2016/202872 | A1 | 12/2016 |
| WO | 2018/096007 | A2 | 5/2018 |
| WO | 2018/096013 | A1 | 5/2018 |

OTHER PUBLICATIONS

Fateh, et al., "New insight into the application of outer membrane vesicles of Gram-negative bacteria."

Fukasawa, L.O., et al., "Neisseria meningitidis serogroup C polysaccharide and serogroup B outer membrane vesicle conjugate as a bivalent meningococcus vaccine candidate." Vaccine; 1999; pp. 2951-2958; vol. 17(23-24).

Gerke, C., et al., "Production of a Shigella sonnei Vaccine Based on Generalized Modules for Membrane Antigens." PLoS One; 2015; pp. e0134478; vol. 10(8).

Gerritzen, et al., "Bioengineering bacterial outer membrane vesicles as vaccine platform." Biotechnology Advances; 2017; pp. 565-574; vol. 35.

Hermanson, Greg T., "Bioconjugate Techniques (3rd Edition): Chapter 11—(Strept)avidin-Biotin Systems." In: "Bioconjugate Techniques"; 2013; pp. 465-507.

Rossi, O., et al, "Toll-Like Receptor Activation by Generalized Modules for Membrane Antigens from Lipid A Mutants of *Salmonella enterica* Serovars Typhimurium and Enteritidis." Clinical and Vaccine Immunology; 2016; pp. 304-314; vol. 23.

Schwechheimer, C., et al., "Outer-membrane vesicles from Gram-negative bacteria: biogenesis and functions." Nature Reviews, Microbiology; 2015; vol. 13(10); pp. 605-619.

Siadat, et al., "Preparation and Evaluation of a New Lipopolysaccharide-based Conjugate as a Vaccine Candidate for Brucellosis." Osong Public Health Res Perspect; 2015; vol. 6(1); pp. 9-13.

Tontini, M. "Characterization of carbohydrate based vaccines." Oct. 26, 2012; Retrieved from the Internet: URL: https://hal.archives-ouvertes.fr/tel-00825838/document; p. 54; figure 34, table 18.

Van De Waterbeemd, et al., "Quantitative Proteomics Reveals Distinct Differences in the Protein Content of Outer Membrane Vesicle Vaccines." Journal of Proteome Research; 2013; vol. 12, No. 4; pp. 1898-1908.

Daleke-Schermerhorn, M. et al., "Decoration of Outer Membrane Vesicles with Multiple Antigens by Using an Autotransporter Approach", Applied and Environmental Microbiology, vol. 80, No. 18, Sep. 15, 2014 (Sep. 15, 2014), pp. 5854-5865.

Joyce, JG., et al., "Isolation, structural characterization, and immunological evaluation of a high-molecular weight exopolysaccharide from *Staphylococcus aureus*", Carbohydrate Research, vol. 338, No. 9, 2003, pp. 903-922.

Qian, F., et al., "Addition of CpG ODN to recombinant Pseudomonas aeruginosa ExoProtein A conjugates of AMA1 and Pfs25 greatly increases the No. of responders", Vaccine, vol. 26, No. 20, May 2008, pp. 2521-2527.

Van De Waterbeemd, B., et al., "Improved production process for native outer membrane vesicle vaccine against Neisseria meningitidis", PlosOne, vol. 8, No. 5, May 2013, p. e65157.

Van Houten, N.E., et al., "Filamentous phage as an immunogenic carrier to elicit focused antibody responses against a synthetic peptide", Vaccine, vol. 24, No. 19, May 2006, pp. 4188-4200.

\* cited by examiner

SEQUENCE LISTING

<160> NUMBER OF SEQ ID NOS: 16

<210> SEQ ID NO 1
<211> LENGTH: 247
<212> TYPE: PRT
<213> ORGANISM: Neisseria meningitidis

<400> SEQUENCE: 1

```
Val Ala Ala Asp Ile Gly Ala Gly Leu Ala Asp Ala Leu Thr Ala Pro
 1               5                  10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205
```

```
Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln
                245

<210> SEQ ID NO 2
<211> LENGTH: 488
<212> TYPE: PRT
<213> ORGANISM: Neisseria meningitidis

<400> SEQUENCE: 2

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
            35                  40                  45

Ala Lys Glu Asp Ala Pro Gln Ala Gly Ser Gln Gly Gln Gly Ala Pro
50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
            115                 120                 125

Asn Gln Ala Thr Asp Ala Gly Glu Ser Ser Gln Pro Ala Asn Gln Pro
    130                 135                 140

Asp Met Ala Asn Ala Ala Asp Gly Met Gln Gly Asp Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
            195                 200                 205

Asn Gly Val Leu Ile Asp Gly Pro Ser Gln Asn Ile Thr Leu Thr His
    210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala
            260                 265                 270

Asp Ser Val Gln Met Lys Gly Ile Asn Gln Tyr Ile Ile Phe Tyr Lys
            275                 280                 285

Pro Lys Pro Thr Ser Phe Ala Arg Phe Arg Arg Ser Ala Arg Ser Arg
    290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335
```

```
Asn Ile Phe Ala Pro Glu Gly Asn Tyr Arg Tyr Leu Thr Tyr Gly Ala
                340                 345                 350

Glu Lys Leu Pro Gly Gly Ser Tyr Ala Leu Arg Val Gln Gly Glu Pro
            355                 360                 365

Ala Lys Gly Glu Met Leu Ala Gly Ala Val Tyr Asn Gly Glu Val
        370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
                405                 410                 415

Asp Ser Gly Asp Asp Leu His Met Gly Thr Gln Lys Phe Lys Ala Ala
                420                 425                 430

Ile Asp Gly Asn Gly Phe Lys Gly Thr Trp Thr Glu Asn Gly Ser Gly
                435                 440                 445

Asp Val Ser Gly Lys Phe Tyr Gly Pro Ala Gly Glu Val Ala Gly
            450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp
                485

<210> SEQ ID NO 3
<211> LENGTH: 362
<212> TYPE: PRT
<213> ORGANISM: Neisseria meningitidis

<400> SEQUENCE: 3

Met Lys His Phe Pro Ser Lys Val Leu Thr Thr Ala Ile Leu Ala Thr
1               5                   10                  15

Phe Cys Ser Gly Ala Leu Ala Ala Thr Ser Asp Asp Val Lys Lys
            20                  25                  30

Ala Ala Thr Val Ala Ile Val Ala Ala Tyr Asn Asn Gly Gln Glu Ile
                35                  40                  45

Asn Gly Phe Lys Ala Gly Glu Thr Ile Tyr Asp Ile Gly Glu Asp Gly
50                  55                  60

Thr Ile Thr Gln Lys Asp Ala Thr Ala Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
            115                 120                 125

Leu Ala Asp Thr Asp Ala Ala Leu Asp Glu Thr Thr Asn Ala Leu Asn
130                 135                 140

Lys Leu Gly Glu Asn Ile Thr Thr Phe Ala Glu Glu Thr Lys Thr Asn
145                 150                 155                 160

Ile Val Lys Ile Asp Glu Lys Leu Glu Ala Val Ala Asp Thr Val Asp
                165                 170                 175

Lys His Ala Glu Ala Phe Asn Asp Ile Ala Asp Ser Leu Asp Glu Thr
            180                 185                 190

Asn Thr Lys Ala Asp Glu Ala Val Lys Thr Ala Asn Glu Ala Lys Gln
            195                 200                 205

Thr Ala Glu Glu Thr Lys Gln Asn Val Asp Ala Lys Val Lys Ala Ala
```

```
              210                 215                 220
Glu Thr Ala Ala Gly Lys Ala Glu Ala Ala Gly Thr Ala Asn Thr
225                 230                 235                 240

Ala Ala Asp Lys Ala Glu Ala Val Ala Ala Lys Val Thr Asp Ile Lys
                245                 250                 255

Ala Asp Ile Ala Thr Asn Lys Ala Asp Ile Ala Lys Asn Ser Ala Arg
                260                 265                 270

Ile Asp Ser Leu Asp Lys Asn Val Ala Asn Leu Arg Lys Glu Thr Arg
            275                 280                 285

Gln Gly Leu Ala Glu Gln Ala Ala Leu Ser Gly Leu Phe Gln Pro Tyr
        290                 295                 300

Asn Val Gly Arg Phe Asn Val Thr Ala Val Gly Gly Tyr Lys Ser
305                 310                 315                 320

Glu Ser Ala Val Ala Ile Gly Thr Gly Phe Arg Phe Thr Glu Asn Phe
                325                 330                 335

Ala Ala Lys Ala Gly Val Ala Val Gly Thr Ser Ser Gly Ser Ser Ala
                340                 345                 350

Ala Tyr His Val Gly Val Asn Tyr Glu Trp
            355                 360

<210> SEQ ID NO 4
<211> LENGTH: 174
<212> TYPE: PRT
<213> ORGANISM: Neisseria meningitidis

<400> SEQUENCE: 4

Met Lys Lys Ala Leu Ala Thr Leu Ile Ala Leu Ala Leu Pro Ala Ala
1               5                   10                  15

Ala Leu Ala Glu Gly Ala Ser Gly Phe Tyr Val Gln Ala Asp Ala Ala
                20                  25                  30

His Ala Lys Ala Ser Ser Ser Leu Gly Ser Ala Lys Gly Phe Ser Pro
            35                  40                  45

Arg Ile Ser Ala Gly Tyr Arg Ile Asn Asp Leu Arg Phe Ala Val Asp
        50                  55                  60

Tyr Thr Arg Tyr Lys Asn Tyr Lys Ala Pro Ser Thr Asp Phe Lys Leu
65                  70                  75                  80

Tyr Ser Ile Gly Ala Ser Ala Ile Tyr Asp Phe Asp Thr Gln Ser Pro
                85                  90                  95

Val Lys Pro Tyr Leu Gly Ala Arg Leu Ser Leu Asn Arg Ala Ser Val
                100                 105                 110

Asp Leu Gly Gly Ser Asp Ser Phe Ser Gln Thr Ser Ile Gly Leu Gly
            115                 120                 125

Val Leu Thr Gly Val Ser Tyr Ala Val Thr Pro Asn Val Asp Leu Asp
        130                 135                 140

Ala Gly Tyr Arg Tyr Asn Tyr Ile Gly Lys Val Asn Thr Val Lys Asn
145                 150                 155                 160

Val Arg Ser Gly Glu Leu Ser Ala Gly Val Arg Val Lys Phe
                165                 170

<210> SEQ ID NO 5
<211> LENGTH: 591
<212> TYPE: PRT
<213> ORGANISM: Neisseria meningitidis

<400> SEQUENCE: 5

Met Asn Lys Ile Tyr Arg Ile Ile Trp Asn Ser Ala Leu Asn Ala Trp
```

-continued

```
1               5                   10                  15
Val Val Val Ser Glu Leu Thr Arg Asn His Thr Lys Arg Ala Ser Ala
                20                  25                  30
Thr Val Lys Thr Ala Val Leu Ala Thr Leu Leu Phe Ala Thr Val Gln
                35                  40                  45
Ala Ser Ala Asn Asn Glu Glu Gln Glu Glu Asp Leu Tyr Leu Asp Pro
            50                  55                  60
Val Gln Arg Thr Val Ala Val Leu Ile Val Asn Ser Asp Lys Glu Gly
65                  70                  75                  80
Thr Gly Glu Lys Glu Lys Val Glu Glu Asn Ser Asp Trp Ala Val Tyr
                    85                  90                  95
Phe Asn Glu Lys Gly Val Leu Thr Ala Arg Glu Ile Thr Leu Lys Ala
                100                 105                 110
Gly Asp Asn Leu Lys Ile Lys Gln Asn Gly Thr Asn Phe Thr Tyr Ser
                115                 120                 125
Leu Lys Lys Asp Leu Thr Asp Leu Thr Ser Val Gly Thr Glu Lys Leu
130                 135                 140
Ser Phe Ser Ala Asn Gly Asn Lys Val Asn Ile Thr Ser Asp Thr Lys
145                 150                 155                 160
Gly Leu Asn Phe Ala Lys Glu Thr Ala Gly Thr Asn Gly Asp Thr Thr
                    165                 170                 175
Val His Leu Asn Gly Ile Gly Ser Thr Leu Thr Asp Thr Leu Leu Asn
                180                 185                 190
Thr Gly Ala Thr Thr Asn Val Thr Asn Asp Asn Val Thr Asp Asp Glu
                195                 200                 205
Lys Lys Arg Ala Ala Ser Val Lys Asp Val Leu Asn Ala Gly Trp Asn
210                 215                 220
Ile Lys Gly Val Lys Pro Gly Thr Thr Ala Ser Asp Asn Val Asp Phe
225                 230                 235                 240
Val Arg Thr Tyr Asp Thr Val Glu Phe Leu Ser Ala Asp Thr Lys Thr
                    245                 250                 255
Thr Thr Val Asn Val Glu Ser Lys Asp Asn Gly Lys Lys Thr Glu Val
                260                 265                 270
Lys Ile Gly Ala Lys Thr Ser Val Ile Lys Glu Lys Asp Gly Lys Leu
            275                 280                 285
Val Thr Gly Lys Asp Lys Gly Glu Asn Gly Ser Ser Thr Asp Glu Gly
                290                 295                 300
Glu Gly Leu Val Thr Ala Lys Glu Val Ile Asp Ala Val Asn Lys Ala
305                 310                 315                 320
Gly Trp Arg Met Lys Thr Thr Ala Asn Gly Gln Thr Gly Gln Ala
                    325                 330                 335
Asp Lys Phe Glu Thr Val Thr Ser Gly Thr Asn Val Thr Phe Ala Ser
                340                 345                 350
Gly Lys Gly Thr Thr Ala Thr Val Ser Lys Asp Gln Gly Asn Ile
                355                 360                 365
Thr Val Met Tyr Asp Val Asn Val Gly Asp Ala Leu Asn Val Asn Gln
            370                 375                 380
Leu Gln Asn Ser Gly Trp Asn Leu Asp Ser Lys Ala Val Ala Gly Ser
385                 390                 395                 400
Ser Gly Lys Val Ile Ser Gly Asn Val Ser Pro Ser Lys Gly Lys Met
                    405                 410                 415
Asp Glu Thr Val Asn Ile Asn Ala Gly Asn Asn Ile Glu Ile Thr Arg
                420                 425                 430
```

Asn Gly Lys Asn Ile Asp Ile Ala Thr Ser Met Thr Pro Gln Phe Ser
            435                 440                 445

Ser Val Ser Leu Gly Ala Gly Ala Asp Ala Pro Thr Leu Ser Val Asp
        450                 455                 460

Gly Asp Ala Leu Asn Val Gly Ser Lys Asp Asn Lys Pro Val Arg
465                 470                 475                 480

Ile Thr Asn Val Ala Pro Gly Val Lys Glu Gly Asp Val Thr Asn Val
                485                 490                 495

Ala Gln Leu Lys Gly Val Ala Gln Asn Leu Asn Asn Arg Ile Asp Asn
            500                 505                 510

Val Asp Gly Asn Ala Arg Ala Gly Ile Ala Gln Ala Ile Ala Thr Ala
        515                 520                 525

Gly Leu Val Gln Ala Tyr Leu Pro Gly Lys Ser Met Met Ala Ile Gly
        530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
            580                 585                 590

<210> SEQ ID NO 6
<211> LENGTH: 1457
<212> TYPE: PRT
<213> ORGANISM: Neisseria meningitidis

<400> SEQUENCE: 6

Met Lys Thr Thr Asp Lys Arg Thr Thr Glu Thr His Arg Lys Ala Pro
1               5                   10                  15

Lys Thr Gly Arg Ile Arg Phe Ser Pro Ala Tyr Leu Ala Ile Cys Leu
            20                  25                  30

Ser Phe Gly Ile Leu Pro Gln Ala Trp Ala Gly His Thr Tyr Phe Gly
        35                  40                  45

Ile Asn Tyr Gln Tyr Tyr Arg Asp Phe Ala Glu Asn Lys Gly Lys Phe
    50                  55                  60

Ala Val Gly Ala Lys Asp Ile Glu Val Tyr Asn Lys Lys Gly Glu Leu
65                  70                  75                  80

Val Gly Lys Ser Met Thr Lys Ala Pro Met Ile Asp Phe Ser Val Val
            85                  90                  95

Ser Arg Asn Gly Val Ala Ala Leu Val Gly Asp Gln Tyr Ile Val Ser
            100                 105                 110

Val Ala His Asn Gly Gly Tyr Asn Asn Val Asp Phe Gly Ala Glu Gly
        115                 120                 125

Arg Asn Pro Asp Gln His Arg Phe Thr Tyr Lys Ile Val Lys Arg Asn
    130                 135                 140

Asn Tyr Lys Ala Gly Thr Lys Gly His Pro Tyr Gly Gly Asp Tyr His
145                 150                 155                 160

Met Pro Arg Leu His Lys Phe Val Thr Asp Ala Glu Pro Val Glu Met
                165                 170                 175

Thr Ser Tyr Met Asp Gly Arg Lys Tyr Ile Asp Gln Asn Asn Tyr Pro
            180                 185                 190

Asp Arg Val Arg Ile Gly Ala Gly Arg Gln Tyr Trp Arg Ser Asp Glu
        195                 200                 205

Asp Glu Pro Asn Asn Arg Glu Ser Ser Tyr His Ile Ala Ser Ala Tyr

```
            210                 215                 220
Ser Trp Leu Val Gly Gly Asn Thr Phe Ala Gln Asn Gly Ser Gly Gly
225                 230                 235                 240

Gly Thr Val Asn Leu Gly Ser Glu Lys Ile Lys His Ser Pro Tyr Gly
                245                 250                 255

Phe Leu Pro Thr Gly Gly Ser Phe Gly Asp Ser Gly Ser Pro Met Phe
            260                 265                 270

Ile Tyr Asp Ala Gln Lys Gln Lys Trp Leu Ile Asn Gly Val Leu Gln
        275                 280                 285

Thr Gly Asn Pro Tyr Ile Gly Lys Ser Asn Gly Phe Gln Leu Val Arg
    290                 295                 300

Lys Asp Trp Phe Tyr Asp Glu Ile Phe Ala Gly Asp Thr His Ser Val
305                 310                 315                 320

Phe Tyr Glu Pro Arg Gln Asn Gly Lys Tyr Ser Phe Asn Asp Asp Asn
                325                 330                 335

Asn Gly Thr Gly Lys Ile Asn Ala Lys His Glu His Asn Ser Leu Pro
            340                 345                 350

Asn Arg Leu Lys Thr Arg Thr Val Gln Leu Phe Asn Val Ser Leu Ser
        355                 360                 365

Glu Thr Ala Arg Glu Pro Val Tyr His Ala Ala Gly Gly Val Asn Ser
    370                 375                 380

Tyr Arg Pro Arg Leu Asn Asn Gly Glu Asn Ile Ser Phe Ile Asp Glu
385                 390                 395                 400

Gly Lys Gly Glu Leu Ile Leu Thr Ser Asn Ile Asn Gln Gly Ala Gly
                405                 410                 415

Gly Leu Tyr Phe Gln Gly Asp Phe Thr Val Ser Pro Glu Asn Asn Glu
            420                 425                 430

Thr Trp Gln Gly Ala Gly Val His Ile Ser Glu Asp Ser Thr Val Thr
        435                 440                 445

Trp Lys Val Asn Gly Val Ala Asn Asp Arg Leu Ser Lys Ile Gly Lys
    450                 455                 460

Gly Thr Leu His Val Gln Ala Lys Gly Glu Asn Gln Gly Ser Ile Ser
465                 470                 475                 480

Val Gly Asp Gly Thr Val Ile Leu Asp Gln Gln Ala Asp Asp Lys Gly
                485                 490                 495

Lys Lys Gln Ala Phe Ser Glu Ile Gly Leu Val Ser Gly Arg Gly Thr
            500                 505                 510

Val Gln Leu Asn Ala Asp Asn Gln Phe Asn Pro Asp Lys Leu Tyr Phe
        515                 520                 525

Gly Phe Arg Gly Gly Arg Leu Asp Leu Asn Gly His Ser Leu Ser Phe
    530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
                565                 570                 575

Thr Thr Gly Asn Asn Asn Ser Leu Asp Ser Lys Lys Glu Ile Ala Tyr
            580                 585                 590

Asn Gly Trp Phe Gly Glu Lys Asp Thr Thr Lys Thr Asn Gly Arg Leu
        595                 600                 605

Asn Leu Val Tyr Gln Pro Ala Ala Glu Asp Arg Thr Leu Leu Leu Ser
    610                 615                 620

Gly Gly Thr Asn Leu Asn Gly Asn Ile Thr Gln Thr Asn Gly Lys Leu
625                 630                 635                 640
```

-continued

Phe Phe Ser Gly Arg Pro Thr Pro His Ala Tyr Asn His Leu Asn Asp
                645                 650                 655

His Trp Ser Gln Lys Glu Gly Ile Pro Arg Gly Glu Ile Val Trp Asp
            660                 665                 670

Asn Asp Trp Ile Asn Arg Thr Phe Lys Ala Glu Asn Phe Gln Ile Lys
        675                 680                 685

Gly Gly Gln Ala Val Val Ser Arg Asn Val Ala Lys Val Lys Gly Asp
    690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn
                725                 730                 735

Cys Val Glu Lys Thr Ile Thr Asp Asp Lys Val Ile Ala Ser Leu Thr
            740                 745                 750

Lys Thr Asp Ile Ser Gly Asn Val Asp Leu Ala Asp His Ala His Leu
        755                 760                 765

Asn Leu Thr Gly Leu Ala Thr Leu Asn Gly Asn Leu Ser Ala Asn Gly
    770                 775                 780

Asp Thr Arg Tyr Thr Val Ser His Asn Ala Thr Gln Asn Gly Asn Leu
785                 790                 795                 800

Ser Leu Val Gly Asn Ala Gln Ala Thr Phe Asn Gln Ala Thr Leu Asn
                805                 810                 815

Gly Asn Thr Ser Ala Ser Gly Asn Ala Ser Phe Asn Leu Ser Asp His
            820                 825                 830

Ala Val Gln Asn Gly Ser Leu Thr Leu Ser Gly Asn Ala Lys Ala Asn
        835                 840                 845

Val Ser His Ser Ala Leu Asn Gly Asn Val Ser Leu Ala Asp Lys Ala
    850                 855                 860

Val Phe His Phe Glu Ser Ser Arg Phe Thr Gly Gln Ile Ser Gly Gly
865                 870                 875                 880

Lys Asp Thr Ala Leu His Leu Lys Asp Ser Glu Trp Thr Leu Pro Ser
                885                 890                 895

Gly Thr Glu Leu Gly Asn Leu Asn Leu Asp Asn Ala Thr Ile Thr Leu
            900                 905                 910

Asn Ser Ala Tyr Arg His Asp Ala Ala Gly Ala Gln Thr Gly Ser Ala
        915                 920                 925

Thr Asp Ala Pro Arg Arg Ser Arg Ser Arg Ser Leu Leu
    930                 935                 940

Ser Val Thr Pro Pro Thr Ser Val Glu Ser Arg Phe Asn Thr Leu Thr
945                 950                 955                 960

Val Asn Gly Lys Leu Asn Gly Gln Gly Thr Phe Arg Phe Met Ser Glu
                965                 970                 975

Leu Phe Gly Tyr Arg Ser Asp Lys Leu Lys Leu Ala Glu Ser Ser Glu
            980                 985                 990

Gly Thr Tyr Thr Leu Ala Val Asn Asn Thr Gly Asn Glu Pro Ala Ser
        995                 1000                1005

Leu Glu Gln Leu Thr Val Val Glu Gly Lys Asp Asn Lys Pro Leu
    1010                1015                1020

Ser Glu Asn Leu Asn Phe Thr Leu Gln Asn Glu His Val Asp Ala
    1025                1030                1035

Gly Ala Trp Arg Tyr Gln Leu Ile Arg Lys Asp Gly Glu Phe Arg
    1040                1045                1050

```
Leu His Asn Pro Val Lys Glu Gln Glu Leu Ser Asp Lys Leu Gly
1055                1060                1065

Lys Ala Glu Ala Lys Lys Gln Ala Glu Lys Asp Asn Ala Gln Ser
1070                1075                1080

Leu Asp Ala Leu Ile Ala Ala Gly Arg Asp Ala Val Glu Lys Thr
1085                1090                1095

Glu Ser Val Ala Glu Pro Ala Arg Gln Ala Gly Gly Glu Asn Val
1100                1105                1110

Gly Ile Met Gln Ala Glu Glu Lys Lys Arg Val Gln Ala Asp
1115                1120                1125

Lys Asp Thr Ala Leu Ala Lys Gln Arg Glu Ala Glu Thr Arg Pro
1130                1135                1140

Ala Thr Thr Ala Phe Pro Arg Ala Arg Arg Ala Arg Arg Asp Leu
1145                1150                1155

Pro Gln Leu Gln Pro Gln Pro Gln Pro Gln Arg Asp Leu
1160                1165                1170

Ile Ser Arg Tyr Ala Asn Ser Gly Leu Ser Glu Phe Ser Ala Thr
1175                1180                1185

Leu Asn Ser Val Phe Ala Val Gln Asp Glu Leu Asp Arg Val Phe
1190                1195                1200

Ala Glu Asp Arg Arg Asn Ala Val Trp Thr Ser Gly Ile Arg Asp
1205                1210                1215

Thr Lys His Tyr Arg Ser Gln Asp Phe Arg Ala Tyr Arg Gln Gln
1220                1225                1230

Thr Asp Leu Arg Gln Ile Gly Met Gln Lys Asn Leu Gly Ser Gly
1235                1240                1245

Arg Val Gly Ile Leu Phe Ser His Asn Arg Thr Glu Asn Thr Phe
1250                1255                1260

Asp Asp Gly Ile Gly Asn Ser Ala Arg Leu Ala His Gly Ala Val
1265                1270                1275

Phe Gly Gln Tyr Gly Ile Asp Arg Phe Tyr Ile Gly Ile Ser Ala
1280                1285                1290

Gly Ala Gly Phe Ser Ser Gly Ser Leu Ser Asp Gly Ile Gly Gly
1295                1300                1305

Lys Ile Arg Arg Arg Val Leu His Tyr Gly Ile Gln Ala Arg Tyr
1310                1315                1320

Arg Ala Gly Phe Gly Gly Phe Gly Ile Glu Pro His Ile Gly Ala
1325                1330                1335

Thr Arg Tyr Phe Val Gln Lys Ala Asp Tyr Arg Tyr Glu Asn Val
1340                1345                1350

Asn Ile Ala Thr Pro Gly Leu Ala Phe Asn Arg Tyr Arg Ala Gly
1355                1360                1365

Ile Lys Ala Asp Tyr Ser Phe Lys Pro Ala Gln His Ile Ser Ile
1370                1375                1380

Thr Pro Tyr Leu Ser Leu Ser Tyr Thr Asp Ala Ala Ser Gly Lys
1385                1390                1395

Val Arg Thr Arg Val Asn Thr Ala Val Leu Ala Gln Asp Phe Gly
1400                1405                1410

Lys Thr Arg Ser Ala Glu Trp Gly Val Asn Ala Glu Ile Lys Gly
1415                1420                1425

Phe Thr Leu Ser Leu His Ala Ala Ala Ala Lys Gly Pro Gln Leu
1430                1435                1440

Glu Ala Gln His Ser Ala Gly Ile Lys Leu Gly Tyr Arg Trp
```

1445          1450          1455

<210> SEQ ID NO 7
<211> LENGTH: 327
<212> TYPE: PRT
<213> ORGANISM: Neisseria meningitidis

<400> SEQUENCE: 7

| Ala | Thr | Asn | Asp | Asp | Val | Lys | Lys | Ala | Thr | Val | Ala | Ile | Ala |
| 1 | | | | 5 | | | | | 10 | | | | 15 |

| Ala | Ala | Tyr | Asn | Asn | Gly | Gln | Glu | Ile | Asn | Gly | Phe | Lys | Ala | Gly | Glu |
| | | | 20 | | | | 25 | | | | | 30 | | | |

| Thr | Ile | Tyr | Asp | Ile | Asp | Glu | Asp | Gly | Thr | Ile | Thr | Lys | Lys | Asp | Ala |
| | | 35 | | | | | 40 | | | | | 45 | | | |

| Thr | Ala | Ala | Asp | Val | Glu | Ala | Asp | Asp | Phe | Lys | Gly | Leu | Gly | Leu | Lys |
| | 50 | | | | | 55 | | | | | 60 | | | | |

| Lys | Val | Val | Thr | Asn | Leu | Thr | Lys | Thr | Val | Asn | Glu | Asn | Lys | Gln | Asn |
| 65 | | | | | 70 | | | | | 75 | | | | | 80 |

| Val | Asp | Ala | Lys | Val | Lys | Ala | Ala | Glu | Ser | Glu | Ile | Glu | Lys | Leu | Thr |
| | | | | 85 | | | | | 90 | | | | | 95 | |

| Thr | Lys | Leu | Ala | Asp | Thr | Asp | Ala | Ala | Leu | Ala | Asp | Thr | Asp | Ala | Ala |
| | | | 100 | | | | | 105 | | | | | 110 | | |

| Leu | Asp | Ala | Thr | Thr | Asn | Ala | Leu | Asn | Lys | Leu | Gly | Glu | Asn | Ile | Thr |
| | | 115 | | | | | 120 | | | | | 125 | | | |

| Thr | Phe | Ala | Glu | Glu | Thr | Lys | Thr | Asn | Ile | Val | Lys | Ile | Asp | Glu | Lys |
| | 130 | | | | | 135 | | | | | 140 | | | | |

| Leu | Glu | Ala | Val | Ala | Asp | Thr | Val | Asp | Lys | His | Ala | Glu | Ala | Phe | Asn |
| 145 | | | | | 150 | | | | | 155 | | | | | 160 |

| Asp | Ile | Ala | Asp | Ser | Leu | Asp | Glu | Thr | Asn | Thr | Lys | Ala | Asp | Glu | Ala |
| | | | | 165 | | | | | 170 | | | | | 175 | |

| Val | Lys | Thr | Ala | Asn | Glu | Ala | Lys | Gln | Thr | Ala | Glu | Glu | Thr | Lys | Gln |
| | | | 180 | | | | | 185 | | | | | 190 | | |

| Asn | Val | Asp | Ala | Lys | Val | Lys | Ala | Ala | Glu | Thr | Ala | Ala | Gly | Lys | Ala |
| | | 195 | | | | | 200 | | | | | 205 | | | |

| Glu | Ala | Ala | Ala | Gly | Thr | Ala | Asn | Thr | Ala | Ala | Asp | Lys | Ala | Glu | Ala |
| | 210 | | | | | 215 | | | | | 220 | | | | |

| Val | Ala | Ala | Lys | Val | Thr | Asp | Ile | Lys | Ala | Asp | Ile | Ala | Thr | Asn | Lys |
| 225 | | | | | 230 | | | | | 235 | | | | | 240 |

| Asp | Asn | Ile | Ala | Lys | Lys | Ala | Asn | Ser | Ala | Asp | Val | Tyr | Thr | Arg | Glu |
| | | | | 245 | | | | | 250 | | | | | 255 | |

| Glu | Ser | Asp | Ser | Lys | Phe | Val | Arg | Ile | Asp | Gly | Leu | Asn | Ala | Thr | Thr |
| | | | 260 | | | | | 265 | | | | | 270 | | |

| Glu | Lys | Leu | Asp | Thr | Arg | Leu | Ala | Ser | Ala | Glu | Lys | Ser | Ile | Ala | Asp |
| | | 275 | | | | | 280 | | | | | 285 | | | |

| His | Asp | Thr | Arg | Leu | Asn | Gly | Leu | Asp | Lys | Thr | Val | Ser | Asp | Leu | Arg |
| | 290 | | | | | 295 | | | | | 300 | | | | |

| Lys | Glu | Thr | Arg | Gln | Gly | Leu | Ala | Glu | Gln | Ala | Ala | Leu | Ser | Gly | Leu |
| 305 | | | | | 310 | | | | | 315 | | | | | 320 |

| Phe | Gln | Pro | Tyr | Asn | Val | Gly |
| | | | | 325 | | |

<210> SEQ ID NO 8
<211> LENGTH: 248
<212> TYPE: PRT
<213> ORGANISM: Neisseria meningitidis

<400> SEQUENCE: 8

```
Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
            180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245
```

<210> SEQ ID NO 9
<211> LENGTH: 250
<212> TYPE: PRT
<213> ORGANISM: Neisseria meningitidis

<400> SEQUENCE: 9

```
Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110
```

Pro Asp Lys Thr Asp Ser Leu Ile Asn Gln Arg Ser Phe Leu Val Ser
            115                 120                 125

Gly Leu Gly Gly Glu His Thr Ala Phe Asn Gln Leu Pro Gly Gly Lys
        130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
            245                 250

<210> SEQ ID NO 10
<211> LENGTH: 171
<212> TYPE: PRT
<213> ORGANISM: Artificial Sequence
<220> FEATURE:
<223> OTHER INFORMATION: Plasmodium falciparum

<400> SEQUENCE: 10

Lys Val Thr Val Asp Thr Val Cys Lys Arg Gly Phe Leu Ile Gln Met
1               5                   10                  15

Ser Gly His Leu Glu Cys Lys Cys Glu Asn Asp Leu Val Leu Val Asn
            20                  25                  30

Glu Glu Thr Cys Glu Glu Lys Val Leu Lys Cys Asp Glu Lys Thr Val
        35                  40                  45

Asn Lys Pro Cys Gly Asp Phe Ser Lys Cys Ile Lys Ile Asp Gly Asn
    50                  55                  60

Pro Val Ser Tyr Ala Cys Lys Cys Asn Leu Gly Tyr Asp Met Val Asn
65                  70                  75                  80

Asn Val Cys Ile Pro Asn Glu Cys Lys Gln Val Thr Cys Gly Asn Gly
                85                  90                  95

Lys Cys Ile Leu Asp Thr Ser Asn Pro Val Lys Thr Gly Val Cys Ser
            100                 105                 110

Cys Asn Ile Gly Lys Val Pro Asn Val Gln Asp Gln Asn Lys Cys Ser
        115                 120                 125

Lys Asp Gly Glu Thr Lys Cys Ser Leu Lys Cys Leu Lys Glu Gln Glu
    130                 135                 140

Thr Cys Lys Ala Val Asp Gly Ile Tyr Lys Cys Asp Cys Lys Asp Gly
145                 150                 155                 160

Phe Ile Ile Asp Gln Glu Ser Ser Ile Cys Thr
                165                 170

<210> SEQ ID NO 11
<211> LENGTH: 630
<212> TYPE: PRT
<213> ORGANISM: Artificial Sequence
<220> FEATURE:
<223> OTHER INFORMATION: Synthetic pfs48/45-GURLP fusion protein
    polypeptide

```
<400> SEQUENCE: 11

Ala Glu Arg Ser Thr Ser Glu Asn Arg Asn Lys Arg Ile Gly Gly Pro
 1               5                  10                  15

Lys Leu Arg Gly Asn Val Thr Ser Asn Ile Lys Phe Pro Ser Asp Asn
             20                  25                  30

Lys Gly Lys Ile Ile Arg Gly Ser Asn Asp Lys Leu Asn Lys Asn Ser
         35                  40                  45

Glu Asp Val Leu Glu Gln Ser Glu Lys Ser Leu Val Ser Glu Asn Val
     50                  55                  60

Pro Ser Gly Leu Asp Ile Asp Ile Pro Lys Glu Ser Ile Phe Ile
 65                  70                  75                  80

Gln Glu Asp Gln Glu Gly Gln Thr His Ser Glu Leu Asn Pro Glu Thr
                 85                  90                  95

Ser Glu His Ser Lys Asp Leu Asn Asn Asn Gly Ser Lys Asn Glu Ser
                100                 105                 110

Ser Asp Ile Ile Ser Glu Asn Asn Lys Ser Asn Lys Val Gln Asn His
                115                 120                 125

Phe Glu Ser Leu Ser Asp Leu Glu Leu Leu Glu Asn Ser Ser Gln Asp
    130                 135                 140

Asn Leu Asp Lys Asp Thr Ile Ser Thr Glu Pro Phe Pro Asn Gln Lys
145                 150                 155                 160

His Lys Asp Leu Gln Gln Asp Leu Asn Asp Glu Pro Leu Glu Pro Phe
                165                 170                 175

Pro Thr Gln Ile His Lys Asp Tyr Lys Glu Lys Asn Leu Ile Asn Glu
                180                 185                 190

Glu Asp Ser Glu Pro Phe Pro Arg Gln Lys His Lys Lys Val Asp Asn
            195                 200                 205

His Asn Glu Glu Lys Asn Val Phe His Glu Asn Gly Ser Ala Asn Gly
        210                 215                 220

Asn Gln Gly Ser Leu Lys Leu Lys Ser Phe Asp Glu His Leu Lys Asp
225                 230                 235                 240

Glu Lys Ile Glu Asn Glu Pro Leu Val His Glu Asn Leu Ser Ile Pro
                245                 250                 255

Asn Asp Pro Ile Glu Gln Ile Leu Asn Gln Pro Glu Gln Glu Thr Asn
                260                 265                 270

Ile Gln Glu Gln Leu Tyr Asn Glu Lys Gln Asn Val Glu Glu Lys Gln
            275                 280                 285

Asn Ser Gln Ile Pro Ser Leu Asp Leu Lys Glu Pro Thr Asn Glu Asp
        290                 295                 300

Ile Leu Pro Asn His Asn Pro Leu Glu Asn Ile Lys Gln Ser Glu Ser
305                 310                 315                 320

Glu Ile Asn His Val Gln Asp His Ala Leu Pro Lys Glu Asn Ile Ile
                325                 330                 335

Asp Lys Leu Asp Asn Gln Lys Glu His Ile Asp Gln Ser Gln His Asn
            340                 345                 350

Ile Asn Val Leu Gln Glu Asn Ile Asn Asn His Gln Leu Glu Pro
        355                 360                 365

Gln Glu Lys Pro Asn Ile Glu Ser Phe Glu Pro Lys Asn Ile Asp Ser
    370                 375                 380

Glu Ile Ile Leu Pro Glu Asn Val Glu Thr Glu Ile Ile Asp Asp
385                 390                 395                 400

Val Pro Ser Pro Lys His Ser Asn His Glu Thr Phe Glu Glu Glu Thr
                405                 410                 415
```

Ser Glu Ser Glu His Glu Glu Ala Val Ser Glu Lys Asn Ala His Glu
                420                 425                 430

Thr Val Glu His Glu Glu Thr Val Ser Gln Glu Ser Asn Pro Glu Lys
            435                 440                 445

Ala Asp Asn Asp Gly Asn Val Ser Gln Asn Ser Asn Asn Glu Leu Asn
        450                 455                 460

Glu Asn Glu Phe Val Glu Ser Glu Lys Ser Glu His Glu Ala Arg Ser
465                 470                 475                 480

Lys Pro Lys Tyr Glu Lys Lys Val Ile His Gly Cys Asn Phe Ser Ser
                485                 490                 495

Asn Val Ser Ser Lys His Thr Phe Thr Asp Ser Leu Asp Ile Ser Leu
            500                 505                 510

Val Asp Asp Ser Ala His Ile Ser Cys Asn Val His Leu Ser Glu Pro
        515                 520                 525

Lys Tyr Asn His Leu Val Gly Leu Asn Cys Pro Gly Asp Ile Ile Pro
530                 535                 540

Asp Cys Phe Phe Gln Val Tyr Gln Pro Glu Ser Glu Glu Leu Glu Pro
545                 550                 555                 560

Ser Asn Ile Val Tyr Leu Asp Ser Gln Ile Asn Ile Gly Asp Ile Glu
                565                 570                 575

Tyr Tyr Glu Asp Ala Glu Gly Asp Asp Lys Ile Lys Leu Phe Gly Ile
            580                 585                 590

Val Gly Ser Ile Pro Lys Thr Thr Ser Phe Thr Cys Ile Cys Lys Lys
        595                 600                 605

Asp Lys Lys Ser Ala Tyr Met Thr Val Thr Ile Asp Ser Ala Arg Ser
    610                 615                 620

His His His His His His
625                 630

<210> SEQ ID NO 12
<211> LENGTH: 394
<212> TYPE: PRT
<213> ORGANISM: Artificial Sequence
<220> FEATURE:
<223> OTHER INFORMATION: Synthetic
    circumsporozoite sequence

<400> SEQUENCE: 12

Met Leu Phe Gln Glu Tyr Gln Cys Tyr Gly Ser Ser Asn Thr Arg
1               5                   10                  15

Val Leu Asn Glu Leu Asn Tyr Asp Asn Ala Gly Thr Asn Leu Tyr Asn
            20                  25                  30

Glu Leu Glu Met Asn Tyr Tyr Gly Lys Gln Glu Asn Trp Tyr Ser Leu
        35                  40                  45

Lys Lys Asn Ser Arg Ser Leu Gly Glu Asn Asp Asp Gly Asn Asn Asn
    50                  55                  60

Asn Gly Asp Asn Gly Arg Glu Gly Lys Asp Glu Asp Lys Arg Asp Gly
65                  70                  75                  80

Asn Asn Glu Asp Asn Glu Lys Leu Arg Lys Pro Lys His Lys Lys Leu
                85                  90                  95

Lys Gln Pro Gly Asp Gly Asn Pro Asp Pro Asn Ala Asn Pro Asn Val
            100                 105                 110

Asp Pro Asn Ala Asn Pro Asn Val Asp Pro Asn Ala Asn Pro Asn Val
        115                 120                 125

Asp Pro Asn Ala Asn Pro Asn Ala Asn Pro Asn Ala Asn Pro Asn Ala

```
                130             135             140
Asn Pro Asn Ala Asn Pro Asn Ala Asn Pro Asn Ala
145             150             155             160

Asn Pro Asn Ala Asn Pro Asn Ala Asn Pro Asn Ala
                165             170             175

Asn Pro Asn Ala Asn Pro Asn Ala Asn Pro Asn Val
            180             185             190

Asp Pro Asn Ala Asn Pro Asn Ala Asn Pro Asn Ala
        195             200             205

Asn Pro Asn Ala Asn Pro Asn Ala Asn Pro Asn Ala
    210             215             220

Asn Pro Asn Ala Asn Pro Asn Ala Asn Pro Asn Ala
225             230             235             240

Asn Pro Asn Ala Asn Pro Asn Ala Asn Pro Asn Ala
                245             250             255

Asn Pro Asn Ala Asn Pro Asn Ala Asn Pro Asn Lys
            260             265             270

Asn Asn Gln Gly Asn Gly Gln Gly His Asn Met Pro Asn Asp Pro Asn
        275             280             285

Arg Asn Val Asp Glu Asn Ala Asn Ala Asn Ala Val Lys Asn Asn
    290             295             300

Asn Asn Glu Glu Pro Ser Asp Lys His Ile Glu Lys Tyr Leu Lys Lys
305             310             315             320

Ile Gln Asn Ser Leu Ser Thr Glu Trp Ser Pro Cys Ser Val Thr Cys
                325             330             335

Gly Asn Gly Ile Gln Val Arg Ile Lys Pro Gly Ser Ala Asn Lys Pro
            340             345             350

Lys Asp Glu Leu Asp Tyr Glu Asn Asp Ile Glu Lys Lys Ile Cys Lys
        355             360             365

Met Glu Lys Cys Ser Ser Val Phe Asn Val Val Asn Ser Ser Ile Gly
    370             375             380

Leu Ile Leu Glu His His His His His His
385             390

<210> SEQ ID NO 13
<211> LENGTH: 12
<212> TYPE: PRT
<213> ORGANISM: Plasmodium falciparum

<400> SEQUENCE: 13

Asn Ala Asn Pro Asn Ala Asn Pro Asn Ala Asn Pro
1               5                   10

<210> SEQ ID NO 14
<211> LENGTH: 134
<212> TYPE: PRT
<213> ORGANISM: Escherichia coli

<400> SEQUENCE: 14

Gln Asp Gln Arg Tyr Ile Ser Ile Arg Asn Thr Asp Thr Ile Trp Leu
1               5                   10                  15

Pro Gly Asn Ile Cys Ala Tyr Gln Phe Arg Leu Asp Asn Gly Gly Asn
                20                  25                  30

Asp Glu Gly Phe Gly Pro Leu Thr Ile Thr Leu Gln Leu Lys Asp Lys
            35                  40                  45

Tyr Gly Gln Thr Leu Val Thr Arg Lys Met Glu Thr Glu Ala Phe Gly
```

```
                50                  55                  60
Asp Ser Asn Ala Thr Arg Thr Thr Asp Ala Phe Leu Glu Thr Glu Cys
 65                  70                  75                  80

Val Glu Asn Val Ala Thr Thr Glu Ile Ile Lys Ala Thr Glu Glu Ser
                 85                  90                  95

Asn Gly His Arg Val Ser Leu Pro Leu Ser Val Phe Asp Pro Gln Asp
                100                 105                 110

Tyr His Pro Leu Leu Ile Thr Val Ser Gly Lys Asn Val Asn Leu Glu
                115                 120                 125

His His His His His His
                130

<210> SEQ ID NO 15
<211> LENGTH: 1487
<212> TYPE: PRT
<213> ORGANISM: Escherichia coli

<400> SEQUENCE: 15

Asp Thr Pro Ser Val Asp Ser Gly Ser Gly Thr Leu Pro Glu Val Lys
  1               5                  10                  15

Pro Asp Pro Thr Pro Thr Pro Glu Pro Thr Pro Glu Pro Thr Pro Asp
                 20                  25                  30

Pro Glu Pro Thr Pro Asp Pro Thr Pro Asp Pro Glu Pro Thr Pro Glu
                 35                  40                  45

Pro Glu Pro Glu Pro Val Pro Thr Lys Thr Gly Tyr Leu Thr Leu Gly
                 50                  55                  60

Gly Ser Gln Arg Val Thr Gly Ala Thr Cys Asn Gly Glu Ser Ser Asp
 65                  70                  75                  80

Gly Phe Thr Phe Thr Pro Gly Asn Thr Val Ser Cys Val Val Gly Ser
                 85                  90                  95

Thr Thr Ile Ala Thr Phe Asn Thr Gln Ser Glu Ala Ala Arg Ser Leu
                100                 105                 110

Arg Ala Val Asp Lys Val Ser Phe Ser Leu Glu Asp Ala Gln Glu Leu
                115                 120                 125

Ala Asn Ser Glu Asn Lys Lys Thr Asn Ala Ile Ser Leu Val Thr Ser
                130                 135                 140

Ser Asp Ser Cys Pro Ala Asp Ala Glu Gln Leu Cys Leu Thr Phe Ser
145                 150                 155                 160

Ser Val Val Asp Arg Ala Arg Phe Glu Lys Leu Tyr Lys Gln Ile Asp
                165                 170                 175

Leu Ala Thr Asp Asn Phe Ser Lys Leu Val Asn Glu Val Glu Asn
                180                 185                 190

Asn Ala Ala Thr Asp Lys Ala Pro Ser Thr His Thr Ser Thr Val Val
                195                 200                 205

Pro Val Thr Thr Glu Gly Thr Lys Pro Asp Leu Asn Ala Ser Phe Val
                210                 215                 220

Ser Ala Asn Ala Glu Gln Phe Tyr Gln Tyr Gln Pro Thr Glu Ile Ile
225                 230                 235                 240

Leu Ser Glu Gly Gln Leu Val Asp Ser Leu Gly Asn Gly Val Ala Gly
                245                 250                 255

Val Asp Tyr Tyr Thr Asn Ser Gly Arg Gly Val Thr Asp Glu Asn Gly
                260                 265                 270

Lys Phe Ser Phe Ser Trp Gly Glu Thr Ile Ser Phe Gly Ile Asp Thr
                275                 280                 285
```

```
Phe Glu Leu Gly Ser Val Arg Gly Asn Lys Ser Thr Ile Ala Leu Thr
290                 295                 300

Glu Leu Gly Asp Glu Val Arg Gly Ala Asn Ile Asp Gln Leu Ile His
305                 310                 315                 320

Arg Tyr Ser Thr Thr Gly Gln Asn Asn Thr Arg Val Val Pro Asp Asp
                325                 330                 335

Val Arg Lys Val Phe Ala Glu Tyr Pro Asn Val Ile Asn Glu Ile Ile
            340                 345                 350

Asn Leu Ser Leu Ser Asn Gly Ala Thr Leu Asp Glu Gly Asp Gln Asn
                355                 360                 365

Val Val Leu Pro Asn Glu Phe Ile Glu Gln Phe Lys Thr Gly Gln Ala
370                 375                 380

Lys Glu Ile Asp Thr Ala Ile Cys Ala Lys Thr Asp Gly Cys Asn Glu
385                 390                 395                 400

Ala Arg Trp Phe Ser Leu Thr Thr Arg Asn Val Asn Asp Gly Gln Ile
                405                 410                 415

Gln Gly Val Ile Asn Lys Leu Trp Gly Val Asp Thr Asn Tyr Gln Ser
            420                 425                 430

Val Ser Lys Phe His Val Phe His Asp Ser Thr Asn Phe Tyr Gly Ser
                435                 440                 445

Thr Gly Asn Ala Arg Gly Gln Ala Val Val Asn Ile Ser Asn Ser Ala
450                 455                 460

Phe Pro Ile Leu Met Ala Arg Asn Asp Lys Asn Tyr Trp Leu Ala Phe
465                 470                 475                 480

Gly Glu Lys Arg Ala Trp Asp Lys Asn Glu Leu Ala Tyr Ile Thr Glu
                485                 490                 495

Ala Pro Ser Ile Val Gln Pro Glu Asn Val Thr Arg Asp Thr Ala Thr
            500                 505                 510

Phe Asn Leu Pro Phe Ile Ser Leu Gly Gln Val Gly Glu Gly Lys Leu
                515                 520                 525

Met Val Ile Gly Asn Pro His Tyr Asn Ser Ile Leu Arg Cys Pro Asn
530                 535                 540

Gly Tyr Ser Trp Gly Gly Val Asn Ser Lys Gly Glu Cys Thr Leu
545                 550                 555                 560

Ser Gly Asp Ser Asp Met Lys His Phe Met Gln Asn Val Leu Arg
                565                 570                 575

Tyr Leu Ser Asn Asp Ile Trp Gln Pro Asn Thr Lys Ser Ile Met Thr
            580                 585                 590

Val Gly Thr Asn Leu Glu Asn Val Tyr Phe Lys Lys Ala Gly Gln Val
                595                 600                 605

Leu Gly Asn Ser Ala Pro Phe Ala Phe His Glu Asp Phe Thr Gly Ile
610                 615                 620

Thr Val Lys Gln Leu Thr Ser Tyr Gly Asp Leu Asn Pro Glu Glu Ile
625                 630                 635                 640

Pro Leu Leu Ile Leu Asn Gly Phe Glu Tyr Val Thr Gln Trp Ser Gly
                645                 650                 655

Asp Pro Tyr Ala Val Pro Leu Arg Ala Asp Thr Ser Lys Pro Lys Leu
            660                 665                 670

Thr Gln Gln Asp Val Thr Asp Leu Ile Ala Tyr Leu Asn Lys Gly Gly
                675                 680                 685

Ser Val Leu Ile Met Glu Asn Val Met Ser Asn Leu Lys Glu Glu Ser
690                 695                 700

Ala Ser Ser Phe Val Arg Leu Leu Asp Ala Ala Gly Leu Ser Met Ala
```

-continued

```
            705                 710                 715                 720
        Leu Asn Lys Ser Val Val Asn Asp Pro Gln Gly Tyr Pro Asp Arg
                        725                 730                 735

Val Arg Gln Arg Arg Ala Thr Gly Ile Trp Val Tyr Glu Arg Tyr Pro
                        740                 745                 750

Ala Ala Asp Gly Ala Gln Pro Pro Tyr Thr Ile Asp Pro Asn Thr Gly
                        755                 760                 765

Glu Val Thr Trp Lys Tyr Gln Gln Asp Asn Lys Pro Asp Lys Pro
                770                 775                 780

Lys Leu Glu Val Ala Ser Trp Gln Glu Val Glu Gly Lys Gln Val
        785                 790                 795                 800

Thr Arg Tyr Ala Phe Ile Asp Glu Ala Glu Tyr Thr Glu Glu Ser
                        805                 810                 815

Leu Glu Ala Ala Lys Ala Lys Ile Phe Glu Lys Phe Pro Gly Leu Gln
                        820                 825                 830

Glu Cys Lys Asp Ser Thr Tyr His Tyr Glu Ile Asn Cys Leu Glu Arg
                        835                 840                 845

Arg Pro Gly Thr Asp Val Pro Val Thr Gly Gly Met Tyr Val Pro Arg
                850                 855                 860

Tyr Thr Gln Leu Asn Leu Asp Ala Asp Thr Ala Lys Ala Met Val Gln
        865                 870                 875                 880

Ala Ala Asp Leu Gly Thr Asn Ile Gln Arg Leu Tyr Gln His Glu Leu
                        885                 890                 895

Tyr Phe Arg Thr Lys Gly Ser Lys Gly Glu Arg Leu Asn Ser Val Asp
                        900                 905                 910

Leu Glu Arg Leu Tyr Gln Asn Met Ser Val Trp Leu Trp Asn Asp Thr
                        915                 920                 925

Lys Tyr Arg Tyr Glu Glu Gly Lys Glu Asp Glu Leu Gly Phe Lys Thr
                        930                 935                 940

Phe Thr Glu Phe Leu Asn Cys Tyr Ala Asn Asp Ala Tyr Ala Gly Gly
        945                 950                 955                 960

Thr Lys Cys Ser Ala Asp Leu Lys Lys Ser Leu Val Asp Asn Asn Met
                        965                 970                 975

Ile Tyr Gly Asp Gly Ser Ser Lys Ala Gly Met Met Asn Pro Ser Tyr
                        980                 985                 990

Pro Leu Asn Tyr Met Glu Lys Pro Leu Thr Arg Leu Met Leu Gly Arg
                        995                 1000                1005

Ser Trp Trp Asp Leu Asn Ile Lys Val Asp Val Glu Lys Tyr Pro
                1010                1015                1020

Gly Ser Val Ser Ala Lys Gly Glu Ser Val Thr Glu Asn Ile Ser
                1025                1030                1035

Leu Tyr Ser Asn Pro Thr Lys Trp Phe Ala Gly Asn Met Gln Ser
                1040                1045                1050

Thr Gly Leu Trp Ala Pro Ala Gln Gln Asp Val Thr Ile Lys Ser
                1055                1060                1065

Ser Ala Ser Val Pro Val Thr Val Thr Val Ala Leu Ala Asp Asp
                1070                1075                1080

Leu Thr Gly Arg Glu Lys His Glu Val Ala Leu Asn Arg Pro Pro
                1085                1090                1095

Arg Val Thr Lys Thr Tyr Leu Glu Ala Asn Gly Glu Val Thr
                1100                1105                1110

Phe Lys Val Pro Tyr Gly Gly Leu Ile Tyr Ile Lys Gly Asp Ser
                1115                1120                1125
```

-continued

Lys Asp Asp Val Ser Ala Asn Phe Thr Phe Thr Gly Val Val Lys
1130                1135                1140

Ala Pro Phe Tyr Lys Asp Gly Glu Trp Lys Asn Asp Leu Asp Ser
1145                1150                1155

Pro Ala Pro Leu Gly Glu Leu Glu Ser Ala Ser Phe Val Tyr Thr
1160                1165                1170

Thr Pro Lys Lys Asn Leu Glu Ala Ser Asn Phe Thr Gly Gly Val
1175                1180                1185

Ala Glu Phe Ala Lys Asp Leu Asp Thr Phe Ala Ser Ser Met Asn
1190                1195                1200

Asp Phe Tyr Gly Arg Asn Asp Glu Asp Gly Lys His Arg Met Phe
1205                1210                1215

Thr Tyr Lys Asn Leu Thr Gly His Lys His Arg Phe Thr Asn Asp
1220                1225                1230

Val Gln Ile Ser Ile Gly Asp Ala His Ser Gly Tyr Pro Val Met
1235                1240                1245

Asn Ser Ser Phe Ser Thr Asn Ser Thr Thr Leu Pro Thr Thr Pro
1250                1255                1260

Leu Asn Asp Trp Leu Ile Trp His Glu Val Gly His Asn Ala Ala
1265                1270                1275

Glu Thr Pro Leu Asn Val Pro Gly Ala Thr Glu Val Ala Asn Asn
1280                1285                1290

Val Leu Ala Leu Tyr Met Gln Asp Arg Tyr Leu Gly Lys Met Asn
1295                1300                1305

Arg Val Ala Asp Asp Ile Thr Val Ala Pro Glu Tyr Leu Asp Glu
1310                1315                1320

Ser Asn Gly Gln Ala Trp Ala Arg Gly Gly Ala Gly Asp Arg Leu
1325                1330                1335

Leu Met Tyr Ala Gln Leu Lys Glu Trp Ala Glu Glu Asn Phe Asp
1340                1345                1350

Ile Lys Gln Trp Tyr Pro Asp Gly Glu Leu Pro Lys Phe Tyr Ser
1355                1360                1365

Asp Arg Lys Gly Met Lys Gly Trp Asn Leu Phe Gln Leu Met His
1370                1375                1380

Arg Lys Ala Arg Gly Asp Asp Val Gly Asn Ser Thr Phe Gly Gly
1385                1390                1395

Lys Asn Tyr Cys Ala Glu Ser Asn Gly Asn Ala Ala Asp Thr Leu
1400                1405                1410

Met Leu Cys Ala Ser Trp Val Ala Gln Ala Asp Leu Ser Glu Phe
1415                1420                1425

Phe Lys Lys Trp Asn Pro Gly Ala Ser Ala Tyr Gln Leu Pro Gly
1430                1435                1440

Ala Thr Glu Met Ser Phe Gln Gly Gly Val Ser Ser Ser Ala Tyr
1445                1450                1455

Ser Thr Leu Ala Ser Leu Lys Leu Pro Lys Pro Glu Lys Gly Pro
1460                1465                1470

Glu Thr Ile Asn Lys Val Thr Glu His Lys Met Ser Ala Glu
1475                1480                1485

<210> SEQ ID NO 16
<211> LENGTH: 414
<212> TYPE: PRT
<213> ORGANISM: Escherichia coli

```
<400> SEQUENCE: 16

Val Ala Asp Gly Gln Gln Ala Tyr Thr Leu Thr Leu Thr Ala Val Asp
1               5                   10                  15

Ser Glu Gly Asn Pro Val Thr Gly Glu Ala Ser Arg Leu Arg Leu Val
            20                  25                  30

Pro Gln Asp Thr Asn Gly Val Thr Val Gly Ala Ile Ser Glu Ile Lys
            35                  40                  45

Pro Gly Val Tyr Ser Ala Thr Val Ser Ser Thr Arg Ala Gly Asn Val
        50                  55                  60

Val Val Arg Ala Phe Ser Glu Gln Tyr Gln Leu Gly Thr Leu Gln Gln
65                  70                  75                  80

Thr Leu Lys Phe Val Ala Gly Pro Leu Asp Ala Ala His Ser Ser Ile
                85                  90                  95

Thr Leu Asn Pro Asp Lys Pro Val Val Gly Gly Thr Val Thr Ala Ile
            100                 105                 110

Trp Thr Ala Lys Asp Ala Asn Asp Asn Pro Val Thr Gly Leu Asn Pro
        115                 120                 125

Asp Ala Pro Ser Leu Ser Gly Ala Ala Ala Gly Ser Thr Ala Ser
    130                 135                 140

Gly Trp Thr Asp Asn Gly Asp Gly Thr Trp Thr Ala Gln Ile Ser Leu
145                 150                 155                 160

Gly Thr Thr Ala Gly Glu Leu Asp Val Met Pro Lys Leu Asn Gly Gln
                165                 170                 175

Asp Ala Ala Ala Asn Ala Ala Lys Val Thr Val Ala Asp Ala Leu
            180                 185                 190

Ser Ser Asn Gln Ser Lys Val Ser Val Ala Glu Asp His Val Lys Ala
            195                 200                 205

Gly Glu Ser Thr Thr Val Thr Leu Val Ala Lys Asp Ala His Gly Asn
        210                 215                 220

Ala Ile Ser Gly Leu Ser Leu Ser Ala Ser Leu Thr Gly Thr Ala Ser
225                 230                 235                 240

Glu Gly Ala Thr Val Ser Ser Trp Thr Glu Lys Gly Asp Gly Ser Tyr
                245                 250                 255

Val Ala Thr Leu Thr Thr Gly Gly Lys Thr Gly Glu Leu Arg Val Met
            260                 265                 270

Pro Leu Phe Asn Gly Gln Pro Ala Ala Thr Glu Ala Ala Gln Leu Thr
        275                 280                 285

Val Ile Ala Gly Glu Met Ser Ser Ala Asn Ser Thr Leu Val Ala Asp
    290                 295                 300

Asn Lys Thr Pro Thr Val Lys Thr Thr Thr Glu Leu Thr Phe Thr Met
305                 310                 315                 320

Lys Asp Ala Tyr Gly Asn Pro Val Thr Gly Leu Lys Pro Asp Ala Pro
                325                 330                 335

Val Phe Ser Gly Ala Ala Ser Thr Gly Ser Glu Arg Pro Ser Ala Gly
            340                 345                 350

Asn Trp Thr Glu Lys Gly Asn Gly Val Tyr Val Ser Thr Leu Thr Leu
        355                 360                 365
```

```
Gly Ser Ala Ala Gly Gln Leu Ser Val Met Pro Arg Val Asn Gly Gln
    370                 375                 380

Asn Ala Val Ala Gln Pro Leu Val Leu Asn Val Ala Gly Asp Ala Ser
385                 390                 395                 400

Lys Ala Glu Ile Arg Asp Met Thr Val Lys Val Asn Asn Gln
                405                 410
```

MULTI-FUNCTIONALIZED NOMV CONJUGATES

CROSS-REFERENCE TO RELATED APPLICATIONS

This application is filed pursuant to 35 U.S.C. § 371 as a United States National Phase Application of International Application No. PCT/EP2018/071482 filed 8 Aug. 2018 which claims priority from GB 1712824.0 filed 10 Aug. 2017.

This invention is in the field of conjugating "native", non-detergent extracted, outer membrane vesicles (nOMV) to a series of different antigens, to form multi functionalized nOMV-antigen conjugates, particularly useful for immunisation.

SEQUENCE LISTING

The instant application contains a Sequence Listing which has been submitted electronically in ASCII format and is hereby incorporated by reference in its entirety. Said ASCII copy, created on Mar. 24, 2023, is named VB66368_US_SL.txt and is 64,910 bytes in size.

BACKGROUND ART

Conjugation of antigens to carriers is an established procedure for improving immunogenicity, especially for saccharides. For instance, bacterial capsular saccharides are naturally T-cell independent antigens which give rise to an immune response that lacks several important properties. Conjugation to a carrier moiety converts these saccharides to T-cell dependent antigens which can then produce an immunological memory effect, and also elicit effective immune responses in young children.

One known source of protein carrier in such conjugates is the Outer Membrane Protein Complex (OMPC) from *N. meningitidis* serogroup B (e.g. see EP-0467714, Merck & co.), which has been included as the carrier in approved *H. influenzae* B conjugate vaccines. OMPC has also been used as the carrier in protein conjugates. According to the prior art, OMPC is conjugated to an antigen via a protein residue, which may be activated or chemically modified in order to better perform the conjugation with the selected antigen.

Wu et al. (PNAS USA 2006; 103(48): 18243-18248) report that conjugation of Pfs25H (a human malarial transmission-blocking protein) to OMPC resulted in a Pfs25H-OMPC conjugate vaccine that was >1,000 times more potent in generating anti-Pfs25H ELISA reactivity in mice than a similar dose of Pfs25H alone. Conjugation of OMPC to Pfs25H protein can be achieved by reacting maleimide-activated Pfs25H with thiolated outer membrane proteins within OMPC (for a general reference see e.g. WO2006/124712), as shown in Scheme 1.

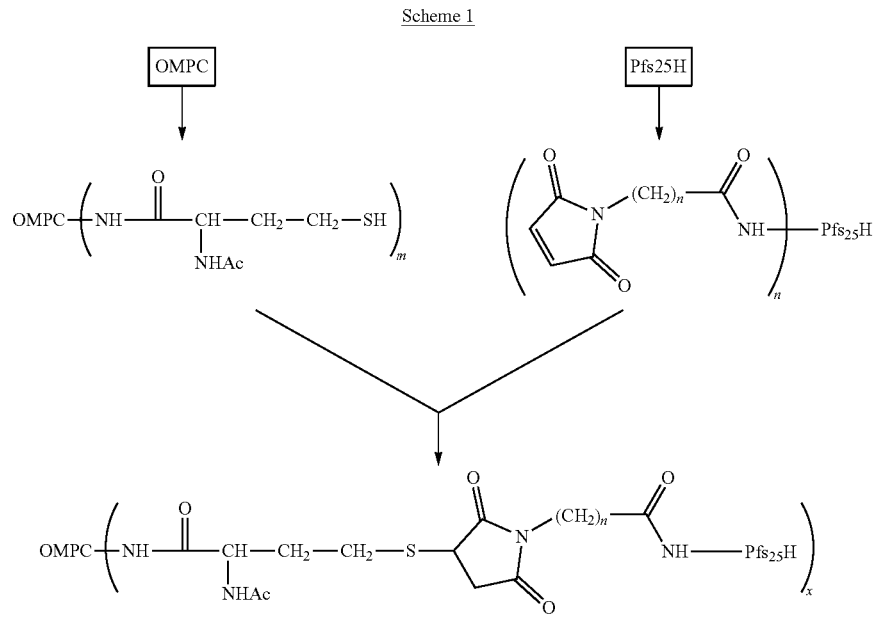

Scheme 1

Even if the process can represent a valid synthetic route, the considered vesicles may be difficult to obtain in a pure form, and they are usually collected via laborious processes. Also, the connection with the selected antigen requires the presence and the activation of a suitable vesicle protein, thus posing an additional challenge in light of the use of detergents or chemicals during the vesicle isolation, that can alter the surface proteins composition. Therefore, there is still the need to provide new conjugates useful as immunogenic compounds which overcome the problems of the prior art, and that are achievable by an easy and convenient procedure.

As shown in the above Scheme 1 and according to general procedures of the prior art, the conjugation methods and derivatives thereof contemplate the use of a bivalent heterobifunctional Linker, i.e. a Linker moiety having the terminal ends bearing different functional groups. This is mainly to avoid the cross linking of the vesicle-Linker intermediate with another vesicle particle rather than with the selected antigen. In practice, according to the prior art, the different ends of the Linker are selected depending on the reactive groups on the vesicle and the selected antigen involved in the process, in order to have a selective reaction with the intended part, namely the vesicle on one side and the antigen on the other end side. These methodologies, however, suffer of some drawbacks, mainly related to the selection and functionalization of the Linkers, thus posing some limitation on the choice of the vesicle and antigen to be coupled together. The Applicant has now found that when native, not detergent extracted Outer Membrane Vesicles (nOMVs) are used as starting vesicles it is possible to use a bivalent Linker suitable for the connection with a nOMV surface protein on one side and with a selected antigen on the other end, thus providing a final derivative that still presents the immunogenic activity of both the nOMV and the antigen. Surprisingly, even when the Linker used in the present invention shows identical terminal functional groups, the conjugation of the nOMV with the selected antigen is achieved substantially without the formation of vesicle aggregates or side products, detrimental for the conjugation reaction.

The Applicant has now also found a new and effective method for the multiple functionalization of nOMV, using different chemical approaches that allow the selective conjugation of chosen antigens.

SUMMARY OF THE INVENTION

In a first aspect, the invention refers to an immunogenic nOMV-antigen conjugate, comprising a native outer membrane vesicle (nOMV) obtained by a detergent free process, having at least a native surface saccharide moiety connected to at least a foreign antigen, and having at least a surface protein residue connected to at least a different foreign antigen through a bivalent Linker.

In a further aspect, the invention refers to a process for preparing said conjugate, comprising the steps of:
i) activating at least a nOMV saccharide moiety, generally bond to the nOMV surface, and
ii) connecting the thus obtained activated nOMV-saccharide to at least one selected antigen, to obtain a nOMV-antigen conjugate;
iii) reacting at least a surface protein residue of the nOMV-antigen conjugate obtained in step ii) with the first terminal portion of a bivalent Linker to obtain a Linker-nOMV-antigen intermediate, and
iv) connecting said Linker-nOMV-antigen intermediate to at least one different antigen via the second terminal portion of the bivalent Linker, thus obtaining the multi-functionalized nOMV derivatives of the invention.

According to the present process, the nOMV-surface bond saccharides are first activated by oxidation, and then reacted with the selected antigen, more preferably under reductive amination conditions. Subsequently, the thus functionalized nOMV is reacted with the linker and then connected through this latter to a different antigen.

The two functionalization mechanisms (via saccharide and via protein/linker as per steps i-ii and iii-iv respectively) can be performed in any order. This means that in an embodiment of the invention the selected nOMV can be first conjugated to an antigen via a nOMV-protein-Linker connection, and subsequently the thus obtained nOMV is conjugated to a different antigen via a surface saccharide moiety. Thus in one embodiment the invention refers to a process for preparing the present conjugates, comprising the steps of:
i) reacting at least a nOMV surface protein residue with the first terminal portion of a bivalent Linker to obtain a nOMV-Linker intermediate, and
ii) connecting said nOMV-Linker intermediate to at least one selected antigen via the second terminal portion of the bivalent Linker, thus obtaining a nOMV-Linker-antigen intermediate,
iii) activating at least a nOMV saccharide moiety of the thus obtained nOMV-Linker-antigen intermediate, and
iv) connecting the thus obtained activated nOMV-saccharide to at least a different antigen, thus obtaining the multi-functionalized nOMV derivatives of the invention.

In an additional aspect, the invention also refers to a conjugate as above set forth, for use as a medicament, particularly as an immunogenic compound, or for the preparation of an immunogenic composition or vaccine.

Still in a further aspect, the invention refers to an immunogenic composition or a vaccine, comprising the above indicated conjugate, and at least one pharmaceutically acceptable carrier or adjuvant; and to a method for raising an immune response in a vertebrate, comprising the administration of said composition or vaccine.

BRIEF DESCRIPTION OF THE DRAWINGS

FIG. 2 confirms the presence of both 405 and 3526 antigens on *S. sonnei* GMMA, where:
1 *E. coli* 405 (2 µg), by using anti-405 primary antibody
2 *S. sonnei* GMMA BS3-405 conjugate (10 µg total protein), by using anti-405 primary antibody
3 (*S. sonnei* GMMA BS3-405)ox-3526 conjugate (10 µg total protein), by using anti-405 primary antibody
4 *E. coli* 3526 (2 µg), by using anti-3526 primary antibody
5 (*S. sonnei* GMMA BS3-405)ox-3526 conjugate (10 µg total protein), by using anti-3526 primary antibody.

DETAILED DESCRIPTION OF THE INVENTION

Figure 1:
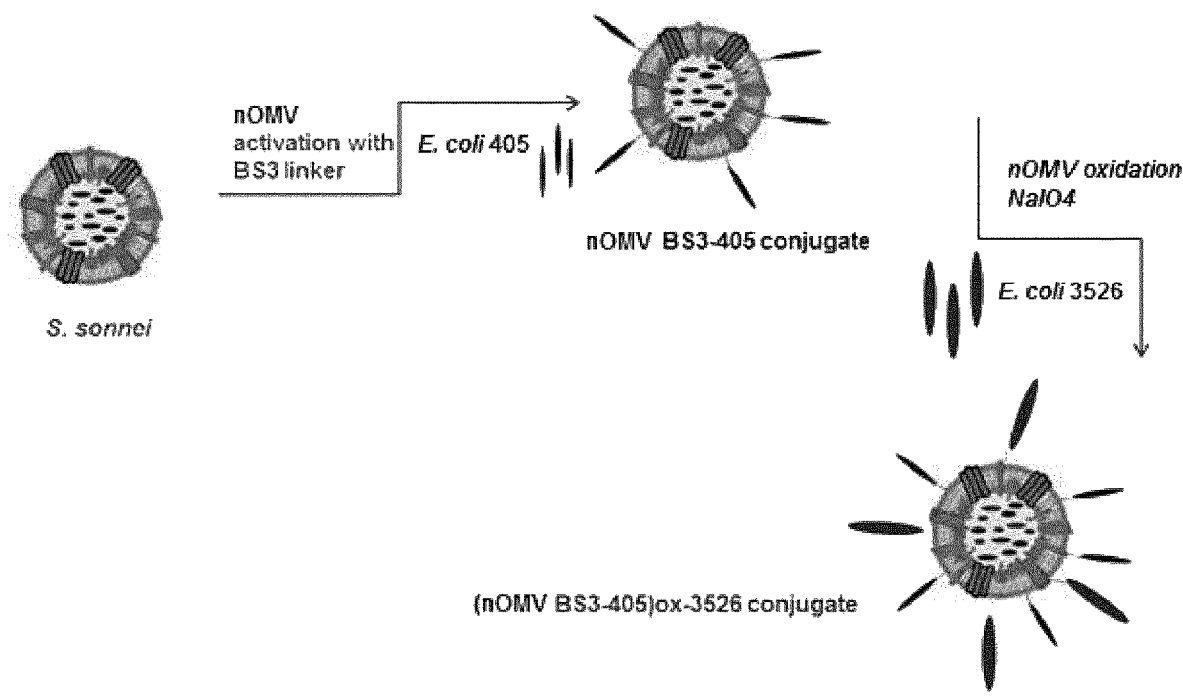
FIG. 1 shows a schematic representation of the conjugation of *E. coli* 405 (FdeC) on *S. sonnei* nOMV by BS3 chemistry, followed by nOMV oxidation and linkage to *E. coli* 3526 (SsIE) by reductive amination according to the present invention. Two orthogonal chemistries have been selected according to the invention, to have linkage of 405 to proteins on nOMV and linkage of 3526 on oxidized LPS on nOMV.

To facilitate an understanding of the present invention, a number of terms and phrases are defined below. Art-recognized synonyms or alternatives of the following terms and phrases (including past, present, etc. tenses), even if not specifically described, are contemplated.

As used in the present disclosure and claims, the singular forms "a," "an," and "the" include plural forms unless the context clearly dictates otherwise; i.e., "a" means "one or more" unless indicated otherwise.

The terms "about" or "approximately" mean roughly, around, or in the regions of. The terms "about" or "approximately" further mean within an acceptable contextual error range for the particular value as determined by one of ordinary skill in the art, which will depend in part on how the value is measured or determined, i.e. the limitations of the measurement system or the degree of precision required for a particular purpose, e.g. the amount of a nutrient within a feeding formulation. When the terms "about" or "approximately" are used in conjunction with a numerical range, it modifies that range by extending the boundaries above and below the numerical values set forth. For example "between about 0.2 and 5.0 mg/ml" means the boundaries of the numerical range extend below 0.2 and above 5.0 so that the particular value in question achieves the same functional result as within the range. For example, "about" and "approximately" can mean within 1 or more than 1 standard deviation as per the practice in the art. Alternatively, "about" and "approximately" can mean a range of up to 20%, preferably up to 10%, more preferably up to 5%, and more preferably up to 1% of a given value.

The term "and/or" as used in a phrase such as "A and/or B" is intended to include "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless specified otherwise, all of the designations "A %-B %," "A-B %," "A % to B %," "A to B %," "A %-B," "A % to B" are given their ordinary and customary meaning. In some embodiments, these designations are synonyms.

The terms "substantially" or "substantial" mean that the condition described or claimed functions in all important aspects as the standard described. Thus, "substantially free" is meant to encompass conditions that function in all important aspects as free conditions, even if the numerical values indicate the presence of some impurities or substances. "Substantial" generally means a value greater than 90%, preferably greater than 95%, most preferably greater than 99%. Where particular values are used in the specification and in the claims, unless otherwise stated, the term "substantially" means with an acceptable error range for the particular value.

An "effective amount" means an amount sufficient to cause the referenced effect or outcome. An "effective amount" can be determined empirically and in a routine manner using known techniques in relation to the stated purpose.

As used herein, "heterologous" means the two or more referenced molecules or structures are derived from a different organism. For example, a heterologous antigen is one that is derived from a different organism than the nOMV vesicle to which it is appended. "Homologous" as used herein means the two or more referenced molecules or structures are derived from the same organism.

As used herein, "foreign" means the two or more referenced molecules or structures are not naturally associated with each other. For example, a selected antigen that is herein intended to be "foreign to" a nOMV herein means the antigen is not naturally or innately conjugated to the nOMV molecule even though the antigen and nOMV molecule may originate from the same organism. In this way, a foreign antigen is not necessarily a heterologous antigen but a heterologous antigen is a foreign antigen.

"Sequence identity" can be determined by the Smith-Waterman homology search algorithm as implemented in the MPSRCH program (Oxford Molecular), using an affine gap search with parameters gap open penalty=12 and gap extension penalty=1, but is preferably determined by the Needleman-Wunsch global alignment algorithm (see e.g. Rubin (2000) Pediatric. Clin. North Am. 47:269-285), using default parameters (e.g. with Gap opening penalty=10.0, and with Gap extension penalty=0.5, using the EBLOSUM62 scoring matrix). This algorithm is conveniently implemented in the needle tool in the EMBOSS package. Where the application refers to sequence identity to a particular SEQ ID, the identity is intended to be calculated over the entire length of that SEQ ID.

The term "w/w %" indicates the weight percentage of a given component, over a different component or over the whole content of a composition, as indicated.

Analogously, the term "% v/v" indicates the volume percentage of a given component, over a different component or over the whole content of a composition, as indicated.

The term "—OAg" (0-antigen) is used within the present invention to indicate an antigen functionality present in the lipopolysaccharides (LPS) or lipooligosaccharides (LOS) on the surface of the considered nOMV, useful for the conjugation with a proper antigen (generally indicated as Ag) according to the invention. In more details, the LPS are generally formed by three different portions, known as: lipidA (responsible for the toxicity of LPS), core oligosaccharide and the —OAg chain, a repetitive glycan polymer and major contributor to the serological specificity of bacteria.

The term "bivalent homobifunctional Linker" or "homologous Linker" indicates a linking unit presenting two terminal ends bearing the same functional group, and able to react with the nOMV protein on one side, and with the selected antigen on the other side, where nOMV protein and selected antigen are as herein below described in details.

Similarly, the term "bivalent heterobifunctional Linker" or "heterologous Linker" indicates a linking unit presenting two terminal ends bearing different functional groups, and able to specifically react with the nOMV protein on one side, and with the selected antigen on the other side, where nOMV protein and selected antigen are as herein below described in details.

The term "linear or branched $C_1$-$C_x$ alkyl or alkenyl group" comprises in its meaning a bivalent satured or unsaturated linear or branched alky or alkenyl group having 1 to x carbon atoms. For instance, the term bivalent $C_1$-$C_{10}$ alkyl or alkenyl group comprises in its meaning a bivalent satured or unsaturated alky or alkenyl group having 1 to 10 carbon atoms such as methyl, ethyl, vinyl, allyl and the like.

As herein used, the term "saccharide (or sugar) moiety" comprises in its meaning mono saccharides, as well as polysaccharide units. It will be appreciated that saccharide moieties can exist in open and closed (ring) form and that, while closed forms are shown in structural formulae herein, open forms are also encompassed by the invention. Similarly, it will be appreciated that saccharide moieties can exist in pyranose and furanose forms and that, while pyranose forms are shown in structural formulae herein, furanose forms are also encompassed. Different anomeric forms of saccharide moieties are also encompassed.

The term "oligosaccharide" comprises in its meaning polysaccharides having from 3 to 10 monosaccharide units.

Unless otherwise provided, the term "polypeptide" refers to polypeptides of any length capable to act as a selected antigen. The amino acid polymer forming the polypeptide of the invention, may be linear or branched, it may comprise modified amino acids, and it may be interrupted by non-amino acids. The term also encompasses an amino acid polymer that has been modified naturally or by intervention; for example, disulphide bond formation, glycosylation, lipidation, acetylation, phosphorylation, or any other manipulation or modification, such as conjugation with a labelling component. Also included within the definition are, for example, polypeptides containing one or more analogues of an amino acid (including, for example, unnatural amino acids, etc.), as well as other modifications known in the art. Polypeptides can occur as single chains or associated chains.

"Average molecular weight" is intended to indicate the average molecular weight obtained by the ordinary arithmetic mean or average of the molecular masses of the individual component, e.g. amino acids in case of polypeptide derivatives.

The term "capsular polysaccharides/saccharides" (CPSs) indicates those saccharides which can be found in the layer that lies outside the cell envelope of bacteria, thus being part of the outer envelope of the bacterial cell itself. CPSs are expressed on the outermost surface of a wide range of bacteria, and in some cases even in fungi.

Unless otherwise provided, the term "conjugation" indicates the connection or linkage of the subjected entities, particularly referred to the nOMV and the selected antigen moieties.

By "immunologically effective amount", it is meant that the administration of that amount to an individual, either in a single dose or as part of a series, is effective for treatment or prevention. This amount can vary depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctors assessment of the medical situation, and other relevant factors. It is expected that the amount will fall in a relatively broad range that can be determined through routine trials.

The term "nOMV" herein indicates vesicle isolated from the medium or sheared from cells, and they are intact membrane vesicles not exposed to detergents or denaturing agents, i.e. not detergent extracted. The nOMVs of the invention present the outer membrane proteins (OMP) and lipopolysaccharide (LPS) in their native conformation and correct orientation in the natural membrane environment, and usually lack the cytoplasmatic components.

On the contrary, the term "OMV" or "dOMV" encompasses a variety of proteoliposomic vesicles obtained by disruption of the outer membrane of a Gram-negative bacterium typically by a detergent extraction process to form vesicles therefrom. Outer membrane protein complexes (e.g. OMPC from *Neisseria meningitidis*) may be considered in such definition, since having three dimensional structure and composition similar to dOMV, and being isolated via detergent extraction procedures (see e.g. EP0467714, U.S. Pat. Nos. 4,271,147, 4,459,286 and 4,830,852). The detergent extraction process removes LPS and phospholipids, together with immunoprotective lipoproteins. Such removal changes the native vesicle structure and promotes aggregation. The aggregation may lead to consequent issues in terms of process development (yield, consistency of production and stability). Differently from nOMVs, characterized by defined homogeneous size distribution (typically in the range 20-250 nm, measured by Dynamic Light Scattering DLS technique), the dOMVs have an undefined heterogeneous size distribution (usually in the range 550-5500 nm as measured by Dynamic Light Scattering DLS technique) caused by detergent-induced vesicle aggregation (see for a general reference, Vaccine 28, 2010, 4810). The detergent extraction process also causes contamination of OMV containing composition (e.g. vaccines) with cytoplasmic proteins as a result of bacterial cell lysis.

According to prior art methodologies, dOMVs and nOMVs may be analysed and described in terms of size, shape and overall appearance of impurities or contaminating non-OMV materials (like vesicle aggregates or detergent residues in case of dOMVs) using the Transmission Electron Microscopy (TEM). For detailed references regarding the differences between dOMVs and nOMVs see e.g. van de Waterbeemd (2013) J. Prot. Res. "Quantitative Proteomics Reveals Distinct Differences in the Protein Content of Outer Membrane Vesicle Vaccines"; and J. Klimentova et al. Microbiological Research 170 (2015) 1-9 "Methods of isolation and purification of the outer membrane vesicles from gram-negative bacteria".

As herein used, unless otherwise provided the term "connection" or "conjugation" means the formation of a covalent bond between the interested entities or moieties.

As above mentioned, the present conjugates are obtained by connecting at least one nOMV surface saccharide moiety to a selected foreign antigen and by covalently connecting at least a protein unit on the same nOMV to a different foreign antigen, via a suitable bivalent Linker.

In this respect, "foreign antigens", means that they do not form part of the vesicle, and typically the antigen connected through saccharide residue is different from the one connected to the surface protein via a bivalent linker. Furthermore, as well as being capable of inducing an immune response against the coupled antigens, the conjugates of the invention are also capable of inducing an immune response against the nOMV component itself, differently from dOMV-antigen conjugates of the art where the immune activity relies mainly on the antigen portion and not on the detergent extracted vesicle. On the contrary, the conjugation of different antigens to the same nOMV according to the present invention does not significantly impact on the ability of the nOMV to induce its own immune response. Of note, when nOMV and the selected foreign antigens are from different sources, the conjugates of the invention may be useful for the preparation of immunogenic compositions or vaccines based on both the nOMV and the conjugated antigens activity. Even further, the possibility to conjugate more than 2 foreign antigens to the same nOMV according to the selective functionalization of the invention is potentially useful for the preparation of a wide range of multivalent nOMV conjugates, endowed with a tailored immunogenic activity.

The nOMVs in accordance with the present invention are collected and isolated substantially without the use of detergents, differently for instance from dOMVs of the prior art obtained via a deoxycholate extraction or using zwitterionic detergents like Empigen BB (see e.g. U.S. Pat. No. 4,707, 543) or similar. On the contrary, it has to be highlighted that a detergent extraction step may be undesirable in the present invention, for a series of reasons, among which the fact that a detergent would reduce the amount of lipopolysaccharide (LPS)/lipooligosaccharide (LOS) present on the vesicle, which can be indeed useful for the conjugation with the selected antigen as herein below described. The conjugates of the invention offer several advantages compared to unconjugated antigens; for example their ability to act as a multivalent vaccine as discussed above, and their improved immunogenicity over unconjugated antigens. In addition, the conjugates of the invention have several advantages over the vesicle-protein conjugates that have been used to date. Firstly, the nOMVs conjugates can be prepared with fewer steps compared to dOMV conjugates in which antigens were coupled to dOMV proteins, and in particular without requiring the expensive and time consuming step of protein derivatisation. Secondly, the production of nOMVs can be more reliable and convenient than the preparation of dOMVs by detergent extraction. Even further, unreacted antigens from the conjugation mixture can be recycled for use in a further conjugation step, improving the efficiency of production of the conjugates.

In further details, the nOMVs are naturally-occurring membrane vesicles that form spontaneously during bacterial growth and are released into culture medium. They can be obtained e.g. by culturing bacteria in broth culture medium, separating whole cells from the smaller nOMVs in the broth culture medium (e.g. by filtration or by low-speed centrifugation to pellet only the cells and not the smaller vesicles), and then collecting the nOMVs from the cell-depleted medium (e.g. by filtration, by differential precipitation or aggregation, by high-speed centrifugation to pellet the vesicles). Strains for use in production of nOMVs can generally be selected on the basis of the amount of nOMVs produced in culture. The present nOMVs are characterised by the fact of being collected and isolated following a detergent-free procedure. Preferably, the present nOMVs are released into the fermentation broth and are purified using a centrifugation and subsequent filtration step (for a general reference see e.g. Clin Vaccine Immunol. 2016 April; 23(4): 304-314). Still preferably, the present nOMVs are released into the fermentation broth and are purified using the following two consecutive Tangential Flow Filtration (TFF) steps: (i) a microfiltration in which the culture supernatant containing the nOMV is separated from the bacteria, and (ii) an ultrafiltration in which the nOMV are separated from soluble proteins (for a general reference see e.g. PLoS One. 2015; 10(8): e0134478). The thus obtained nOMVs can then directly be used within the present invention without additional purification/isolation steps. The presently considered nOMVs have a preferred size distribution comprised from 20 to 250 nm, measured by Dynamic Light Scattering DLS technique.

According to some embodiments, the nOMVs are prepared from wild-type bacteria or from bacteria which have been genetically manipulated generally to increase immunogenicity (e.g. to hyper-express immunogens), to reduce toxicity, to inhibit capsular saccharide synthesis, to down-regulate immunodominant antigen expression, and the like. They also may be prepared from hyperblebbing strains. The nOMVs of the invention may also express exogenous proteins on their surface and they may be endotoxin-depleted.

Preferably, the nOMVs suitable for the invention are produced from genetically-modified bacterial strains that are mutated to enhance vesicle production, and optionally also to remove or modify antigens (e.g. lipid A) and/or to over-express homologous antigens or antigens from other organisms. Said preferred nOMVs are also known as Generalized Modules of Membrane Antigens (GMMA) as e.g. described in PLoS One. 2015; 10(8): e0134478.

Enhanced spontaneous generation of vesicles can be achieved, for example, by targeted deletion of proteins involved in maintenance of membrane integrity. It has been observed that the outer surface of nOMVs substantially corresponds to the outer surface of the bacterium from which they are derived, preserving the membrane antigens (including e.g. lipopolysaccharides, lipooligosaccharides and lipoproteins) in the context of the membrane. Advantageously, the nOMVs used in the invention (unlike detergent-extracted dOMVs) retain these outer membrane components in their native conformation and correct orientation, better preserving immunogenicity against the bacterial strain from which they are derived.

Generally, the nOMVs suitable for the invention may be prepared from any suitable bacterium, where preferred bacteria include, but are not limited to: *Neisseria* (e.g. in particular *N. meningitidis* of any serogroups including A, B, C, X, Y or W135, or from a non-pathogenic *Neisseria*), *Shigella* (such as *S. sonnei*, *S. flexneri*, *dysenteriae* or *boydii*), *Salmonella enterica* serovars (such as Paratyphi A, B or C, *Enteritidis*, *Typhi* or *Typhimurium*), *Haemophilus influenzae* (e.g. non-typable *H. influenzae*), *Vibrio cholerae*, *Bordetella pertussis*, *Mycobacterium smegmatis*, *Mycobacterium bovis* BCG, *Escherichia coli*, *Bacteroides* (including *Porphyromonas*), *Pseudomonas aeruginosa*, *Helicobacter pylori*, *Brucella melitensis Campylobacter jejuni*, *Actinobacillus actinomycetemcomitans*, *Xenorhabdus nematophilus*, *Moraxella catarrhalis*, or *Borrelia burgdorferi*.

Particularly preferred bacteria are selected from at least one of: *S. sonnei*, *S. flexneri*, *Salmonella* bacterium, and meningococcus, particularly meningococcus serogroup B.

Virulent *Shigella* strains possess a 220 kb plasmid that mediates virulence properties. This "virulence plasmid" has been shown to encode the genes for several aspects of *Shigella* virulence, including adhesins for target epithelial cells, the invasion plasmid antigens, virF, virG, and the like. A *Shigella* used with the invention may or may not possess a virulence plasmid. Absence of the plasmid can stabilise the strain during industrial culture, attenuate the strain by removing virulence factors (thereby increasing safety of manufacture), avoid the presence of the ShET-2 enterotoxin (encoded by the ospD3 or sen gene on the plasmid), and avoid the presence of msbB2 which is a second copy of the msbB gene responsible for acylation of lipid A. Absence of the virulence plasmid may also disrupt the lipopolysaccharide. However, the biosynthesis genes for the —OAg should preferably be retained, either by maintenance of a mutated virulence plasmid, or by inclusion in a further plasmid or cloning into the bacterial chromosome.

As far as *Salmonella* bacterium is concerned, a particularly preferred strain is selected from: *Salmonella Typhimurium*, *Salmonella Enteritidis* and *Salmonella* Paratyphi A.

Meningococcus bacteria nOMVs are also preferred. Such vesicles can be prepared from any meningococcal strain. The vesicles are preferably prepared from a serogroup B strain, but it is also preferred to prepare them from serogroups other than B, such as one of: A, C, W135 or Y, according to procedures known in the art. The strain may be of any serotype (e.g. 1, 2a, 2b, 4, 14, 15, 16, etc.), any serosubtype (e.g. P1.4), and any immunotype (e.g. L1; L2; L3; L3,7; L3,7,9; L10; etc.). The meningococci may be from any suitable lineage, including hyperinvasive and hypervirulent lineages, preferably any of the following seven hypervirulent lineages: subgroup I; subgroup III; subgroup IV-1; ET-5 complex; ET-37 complex; A4 cluster; lineage 3. Most preferably, OMVs are prepared from the strain NZ98/254, or another strain with the P1.4 PorA serosubtype.

In another embodiment, bacteria for preparing nOMVs suitable for the invention may be mutant strains which have been manipulated e.g. to enhance vesicle production, to express one or more desired antigen(s), and/or to knockout or modify an undesired gene (e.g. one which encodes a toxin or which encodes an enzyme involved in generating a toxic product, such as endotoxin).

In this direction, other preferred nOMVs suitable for the invention are produced by a *Salmonella* bacterium, particularly a *S. Typhimurium* (also known as *Salmonella enterica* serovar *Typhimurium*) which does not express a functional TolR protein.

Where the vesicles are prepared from *E. coli, Shigella* or *Salmonella* the bacterium may express no more than 4 of TolA, TolB, TolQ, TolR and Pal proteins. Thus at least one protein from the natural five-protein Tol-Pal system may be absent, resulting in a bacterium which, during growth in culture medium, releases greater quantities of outer membrane vesicles into the medium than the same bacterium expressing all 5 Tol-Pal proteins. Preferably TolR is not expressed, but the other four proteins may be expressed (i.e. a ΔTolR strain).

In preferred embodiments, at least one of the five Tol-Pal proteins in *E. coli, Shigella* or *Salmonella* is removed e.g. by deletion or inactivation of the gene encoding the protein. Thus the bacterium may express 0, 1, 2, 3 or 4 of TolA, TolB, TolQ, TolR and Pal proteins. Removal of one of the five proteins can suffice, in which case the bacterium expresses only 4 of these proteins. Preferably the TolR protein is removed e.g. by inactivation of a starting strain's tolR gene. Thus a preferred bacterium may be tolA+ tolB+ tolQ+ TolR− Pal+.

In some embodiments, the bacterium expresses all five Tol-Pal proteins, but at least one is mutated to cause hyperblebbing. For instance, the TolA, TolQ, TolR and/or Pal protein may be mutated such that the protein retains its membrane localisation but its interactions with other members of the Tol-Pal system are disrupted. The bacterium will thus retain TolA, TolQ and TolR as transmembrane proteins in the inner membrane, and Pal protein as a periplasm-facing lipoprotein in the outer membrane, but at least one of the TolA, TolQ, TolR and/or Pal proteins is mutated and not fully functional.

In addition other mutations may also be present e.g. to give OAg-deficient strains, for instance in those cases where the —OAg functionality is not intended for desired immune response, or in those cases where the —OAg may negatively impact the immunogenicity against the heterologous antigen. In this direction, possible mutations may be ΔgalU, ΔgalE or ΔwbaP in *E. coli, Shigella* or *Salmonella* strains.

In one further preferred embodiment, a meningococcus does not express a functional MltA protein. Knockout of MltA (the membrane-bound lytic transglycosylase, also known as GNA33) in meningococcus provides bacteria which spontaneously release large amounts of nOMVs into culture medium, from which they can be readily purified. For instance, the vesicles can be purified using the two stage size filtration process, comprising: (i) a first filtration step in which vesicles are separated from the bacteria based on their different sizes, with the vesicles passing into the filtrate; and (ii) a second filtration step in which the vesicles are retained in the retentate.

In the present invention, it is preferred that —OAg is present on the nOMVs because it has been observed (e.g. nOMVs from *Salmonella* and *Shigella*) that, the presence of the —OAg on the surface of said nOMVs is advantageous in providing a multivalent vaccine, as the —OAg can act as a protective antigen. Some preferred strains have penta- or tetra-acylated less toxic LPS, which includes attached —OAg, after the mutation of msbB, htrB, ddg and/or PagP (see e.g. Rossi O et al, Clin Vaccine Immunol. 2016 Apr. 4; 23(4):304-14 and Rossi 0 et al, J Biol Chem. 2014 Sep. 5; 289(36):24922-35.

In *Neisseria*, the strain has preferably a modified fur gene. According to this embodiment, mutant *Neisseria* are engineered to reduce or switch off expression of at least one gene involved in rendering toxic the lipid A portion of LPS, in particular of Ipx11 gene. In this way, the resulting nOMVs present a reduced toxicity respect to the wild type strain, since the conversion of acylated lipid A in a less acylated form.

Similarly, preferred mutant *Neisseria* for the invention are engineered to reduce or switch off expression of at least one gene involved in the capsular saccharide synthesis or export, in particular of synX and/or ctrA genes. In this way, the resulting nOMVs may present a cross protection versus different serotypes, particularly appreciated by the skilled in the art.

In preferred embodiments a strain may include one or more of the knockout and/or hyper-expression mutations disclosed e.g. in Fukusawa et al. (1999), Vaccine 17:2951-2958. For instance, following the therein guidance and nomenclature, useful genes for down-regulation and/or knockout include: (a) Cps, CtrA, CtrB, CtrC, CtrD, FrpB, GalE, HtrB/MsbB, LbpA, LbpB, LpxK, Opa, Opc, PDC, PorB, SiaA, SiaB, SiaC, SiaD, TbpA, and/or TbpB; (b) CtrA, CtrB, CtrC, CtrD, FrpB, GalE, HtrB/MsbB, LbpA, LbpB, LpxK, Opa, Opc, PhoP, PDC, PmrE, PmrF, SiaA, SiaB, SiaC, SiaD, TbpA, and/or TbpB; (c) ExbB, ExbD, rmpM, CtrA, CtrB, CtrD, GalE, LbpA, LpbB, Opa, Opc, PDC, PorB, SiaA, SiaB, SiaC, SiaD, TbpA, and/or TbpB; or (d) CtrA, CtrB, CtrD, FrpB, OpA, OpC, PilC, PorB, SiaD, SynA, SynB, SynX and/or SynC.

As far as the nOMV saccharide moiety is concerned, it has to be noted that it can be part of the —OAg functionality naturally present on the surface of the nOMV (e.g. in LPS or LOS), or it can be present within a different nOMV surface portion, e.g. a CPS, as herein below described in details. Advantageously, any proper antigen may be conjugated to the nOMV to obtain the nOMV-antigen conjugates of the invention, preferably in the form of a (poly)saccharide or polypeptide. In any case, the connection of one or more selected antigens produces an immunogenic conjugate which can raise an immune response which recognises said antigens, and which also recognises one or more components in the nOMV, thereby conveniently providing a multivalent vaccine. Generally, antigens will be included in the present conjugates at a concentration which is high enough to elicit, when administered to a host, an immune response which recognises that antigen.

As far as the functionalization of the nOMV through a surface protein is concerned, the present invention surprisingly shows that a homobifunctional Linker can be used in the preparation of nOMV-antigen conjugates, without incurring in the prior art problems related e.g. to vesicles cross reaction or aggregation. In practice, the nOMV is functionalized with the homobifunctional Linker by reacting proper functional groups of at least one nOMV surface protein with one end of the Linker. By that, a nOMV-Linker intermediate is covalently formed, still having the other end of the Linker available for the subsequent reaction with the selected antigen. Thus, the second end of the Linker will react with the selected antigen, in a specific and selective way, leading to the final nOMV-Linker-antigen derivative, and substantially avoiding intermediate cross reactions or aggregations. This is particularly valuable since the selective functionalization can be performed on a nOMV already conjugated to a first different antigen, or according to another embodiment of the invention, the firstly obtained nOMV-Linker-Antigen intermediate can undergo a second selective conjugation to a different antigen, via a nOMV polysaccharide, to give the conjugates of the invention. As indicated in the present experimental part, the same functionalization when carried out considering a dOMV as starting vesicle leads to the formation of vesicle-Linker-vesicle aggregates, which are not suitable for a subsequent reaction with the selected antigen. Surprisingly it has now found that not only the use of nOMV as starting vesicle can overcome the aggregation problems of the prior art, but also it is now possible to use a variety of bifunctional Linkers that lead to the preparation of a series of nOMV-antigens derivatives according to the invention, retaining the immunogenic profile of the conjugated components. Of note, the functionalization of the nOMV through the surface protein as just set forth can be performed before or after the functionalization of the nOMV with a different antigen through a saccharide moiety, providing in any case effective and useful multi-functionalized nOMV derivatives.

The nOMVs are covalently linked to the bifunctional Linker by way of at least one protein residue, generally located on the surface of the vesicle. In this direction, the proteins will preferably react with a terminal end of the Linker by means of one or more amino, thiol or hydroxyl amino acid functionalities, being this latter an alpha hydroxyl group or part of the carboxy aminoacid functionality. Preferably, the protein functional group is an amino group, more preferably a primary amine ($-NH_2$). These functional groups may naturally be present in the amino acid portions of interest, or even introduced artificially for the purposes of conjugation. When the selected Linker is a homobifunctional bivalent Linker, it will be understood that the proteins functional group and the antigen functional group that will react with the terminal portion of the Linker will be preferably the same. By way of example, lysine aminoacid residues of one or more nOMV proteins will react with the Linker (e.g. $BS^3$) via the corresponding $-NH_2$ functional group. In the same way, also a selected antigen (e.g. E. coli 405) will react with the remaining free terminal portion of the Linker via the relevant amino ($-NH_2$) groups. Of note, and as well explained in the present description, the reaction occurs without substantial cross reaction or aggregation formation, thus leading to the final product, useful for the preparation of multivalent vaccines, in a very reliable and versatile way, and differently from using dOMVs, as indicated in the comparative Examples herein provided. Preferred amino acid residues include, but are not limited to: arginine, lysine, asparagine, glutamine, aspartic or glutamic acid, cysteine and histidine. Preferably, the nOMV proteins are those having one or more aminoacid moiety showing free amino groups, preferably primary $-NH_2$ groups. Even more preferably said aminoacid moiety is the arginine and/or lysine, whereby different $-NH_2$ groups form different arginine and/or lysine proteins are able to selectively react with the linker according to the present invention.

As far as the bivalent Linker is concerned, this is typically a molecule of a certain length, with a suitable water solubility and polarity able to covalently bind the nOMV proteins and the antigen by its terminal ends respectively. In order to optimize the solubility of the chosen Linker, it may be expedient to introduce one or more polar group such as sulfate, sulfite, phosphate and the like, or even use the corresponding salt thereof, e.g. as alkaline or alkaline earth metal salts, where possible. Due to the versatility of the present invention, it is possible to use different Linkers, in terms e.g. of lengths, polarity, and steric hindrance, thus providing a covalent bond with both the nOMV protein residues and the selected antigen. By that, the invention allows the preparation of a variety of nOMV-Linker-antigens conjugates, endowed with remarkable and specific behavior, with particular regard to their immunogenicity and activity.

The Linker can be heterobifunctional (i.e. bearing two different terminal functionalities) or, preferably homobifunctional (i.e. having equal terminal functionalities). Even more preferably, the Liker is symmetric with respect to a hypothetical vertical axis.

Thus the bivalent Linker according to the present invention has a general formula (I):

$$X\text{-}L\text{-}X'\qquad\qquad(I)$$

wherein:
X and X' are different to each other or the same, and are a functional group able to selectively react with nOMV proteins on one hand and with the selected antigen on the other hand, preferably by forming ester, amido or thioester moieties;
-L- is a bivalent linear or branched $C_1$-$C_{15}$ alkyl or alkenyl group optionally substituted, and optionally interrupted by one or more heteroatom selected from: oxygen ($-O-$), sulfur ($-S-$), nitrogen ($-NH-$ or optionally substituted $-N-$ group) and the like.

In one embodiment, -L- is preferably a bivalent linear C3-C12 alkyl group, optionally substituted or interrupted by one or more oxygen ($-O-$) heteroatom. In a still more preferred embodiment, -L- is a bivalent linear $C_3$-$C_6$ alkyl group. According to formula (I), the Linker is further characterized by having both terminal portions bearing two functionalities X and X' which are preferably the same thus providing a bivalent homo-functional Linker. In one embodiment, the X and/or X' groups can be any which form esters, thioester or amide when combined with a hydroxyl, thiol or amino functionality respectively.

Preferably, X and/or X' are N-hydroxysuccinimide ester derivatives, more preferably selected from at least one of:

wherein the * represents the point of contact with the -L- spacer in formula (I), as above defined.

Thus, in a still preferred embodiment, the Linker is selected from at least one of: disuccinimidyl glutarate (DSG), disuccinimidyl suberate (DSS), succinimidyl 3-(2-pyridyldithio)propionate (SPDP), Succinimidyl 6-(3-[2-pyridyldithio]-propionamido)hexanoate (LC-SPDP), sulfosuccinimidyl 6-(3'-(2-pyridyldithio)propionamido)hexanoate (sulfo-LC-SPDP), 4-succinimidyloxycarbonyl-α-methyl-α-(2-pyridyldithio)toluene (SMPT), sulfosuccinimidyl-6-[α-methyl-α-(2-pyridyldithio)tolueamideo]hexanoate (sulfo- LC-SMPT), succinimidyl 4-(N-maleimidomethyl) cyclohexane-1-carboxylate (SMCC), sulfosuccinimidyl 4-(N-maleimidomethyl)cyclohexane-1-carboxylate (suflo-SMCC), m-maleimidobenzoyl-N-hydroxysuccinimide ester (MBS), m-maleimidobenzoyl-N-hydroxysulfosuccinimide ester (sulfo-MBS), N-succinimidyl (4-iodoacetyl)aminobenzoate (STAB), sulfosuccinimidyl (4-iodoacetyl)aminobenzoate (sulfo-SIAB), succinimidyl 4-(N-maleimidophenyl)butyrate (SMPB), sulfosuccinimidyl 4-(N-maleimidophenyl)butyrate(sulfo-SMPB), N-γ-maleimidobutyryl-oxysuccinimide ester (GMBS), N-γ-maleimidobutyryl-oxysulfosuccinimide ester (sulfo-GMBS), succinimidyl-6-((((4-(iodoacetyl)amino)methyl) cyclohexane-1-carbonyl)amino)hexanoate (SIACX), succinimidyl 6[6-(((iodoacetyl)amino)hexanoyl)amino] hexanoate (SIAXX), succinimidyl-4-(((iodoacetyl)amino) methyl)cyclohexane-1-carboxylate (SIAC), succinimidyl 6-[(iodoacetyl)amino]hexanoate (SIAX) and p-nitrophenyl iodoacetate (NPIA), N-hydroxysuccinimide, N oxysuccinimide and adipic acid N-hydroxysuccinimide diester (SIDEA) and Bis(sulfosuccinimidyl) suberate (BS3, CAS No. 82436-77-9).

In one embodiment, additional preferred bifunctional Linkers reactive with amines for use with the invention are selected from at least one of: acryloyl halides (e.g. chloride), ethylene glycol bis[succinimidylsuccinate], bis(sulfosuccinimidyl)tri(ethylene glycol) (BS(PEG)3), bis(sulfosuccinimidyl)tetra(ethylene glycol) (BS(PEG)4), bis(sulfosuccinimidyl)penta(ethylene glycol) (BS(PEG)5) and bis (sulfosuccinimidyl)exa(ethylene glycol) (BS(PEG)6), where bis(sulfosuccinimidyl)penta(ethylene glycol) (BS (PEG)5, CAS No 756526-03-1) is particularly preferred.

Preferred homobifunctional Linkers able to react with thiol functional groups on nOMV protein and antigen according to the invention, are those having X and/or X' selected from at least one of: 2-pyridyldithio, maleimide or iodoacetyl residue.

Other Linkers suitable for the reaction with the nOMV protein hydroxyl group as above defined, are selected from at least one of: Adipic acid dihydrazide (ADH), 8-propionamido, nitrophenyl-ethylamine, haloacyl halides, 6-aminocaproic acid.

Among the Linkers useful within the present invention, (BS(PEG)5), Disuccinimidyl glutarate (DSG) or a salt thereof, and BS3 are preferred ones, being BS3 even more preferred (for a general reference on BS3 see e.g. U.S. Pat. No. 4,965,338). According to a still preferred embodiment, DSG is particularly useful when operating at pH of about 9. Surprisingly, the efficacy of the conjugation reaction can be conveniently increased when (BS(PEG)5) or BS3 are used as bivalent Linker, substantially in the absence of vesicle aggregates formation. In this respect, it has to be highlighted that the use of BS3 according to the present invention does not provide substantial crosslinking of nOMV surface proteins to form high-molecular-mass aggregates, but rather, selective reaction with nOMV on one terminal end, and with the selected antigen on the other end. This behavior is further supported by the herein enclosed experimental part, where example 4 (comparative, using dOMV) is described.

In one embodiment of the invention, the nOMV is conjugated to at least one homologous antigen, i.e. derived from the same organism from which the nOMVs are derived. In a still preferred embodiment, the nOMV is conjugated to at least one heterologous antigen i.e. derived from a different organism from the organism from which the nOMVs are derived. In any case, the antigens may generally be selected from any immunogenic polypeptides, i.e. polypeptides able to elicit an immune response when administered to a subject. Polypeptides used with the invention will include an amino acid having a residue, or a side chain, with a functional group suitable for conjugation, preferably an amino or a thiol group, even more preferably of general formula: —NH$_2$ or —SH. These residues may naturally be present in an antigen, or they may be introduced artificially for the purposes of conjugation. Preferred amino acid residues include, but are not limited to: arginine, lysine, asparagine, glutamine, cysteine and histidine. The most preferred amino acid residue for conjugation is lysine.

Polypeptide antigens suitable for the invention are preferably prepared in substantially pure or substantially isolated form (i.e. substantially free from other polypeptides). They can be prepared by various means e.g. by chemical synthesis (at least in part), by digesting longer polypeptides using proteases, by translation from RNA, by purification from cell culture (e.g. from recombinant expression or from native culture), and the like. Recombinant expression in an *E. coli* host is a useful expression route. Polypeptide antigens can take various forms (e.g. native, fusions, glycosylated, non-glycosylated, lipidated, disulfide bridges and the like).

Polypeptide antigens suitable for the invention have a preferred average molecular weight of at least 1 kDa, more preferably of at least 3.5 kDa, even more preferably from 10 to 180 kDa, still more preferably, the average molecular weight is comprised from 15 to 75 kDa.

Further preferred polypeptide antigens for conjugating to nOMVs according to the present invention comprise an epitope from a fungal, bacterial, protozoan or viral polypeptide. Preferred protozoan polypeptides are from a *Plasmodium* (such as *P. falciparum, P. vivax, P. ovale*).

Particularly preferred bacterial polypeptides are selected from: *E. coli, N. meningitidis*, and Streptococci (such as *S. agalactiae, S. pneumoniae, S. pyogenes*).

Preferred *E. coli* polypeptide antigens include CTF1232, 405 (FdeC) and 3526 (SsIE). As a non-limiting preferred example, nOMV from *Shigella* can be conjugated to 405 and 3526, according to the present invention, to generate a multivalent vaccine covering both *E. coli* and *Shigella*. In one embodiment, the considered *N. meningitidis* polypeptides are able, when administered to a mammal, to elicit an antibody response that is bactericidal against meningococcus. Preferred *N. meningitidis* polypeptides for use with the invention are selected from at least one of: NHBA, NadA, NspA, NhhA, App and fHbp, as herein below detailed.

*E. coli* 3526 (SsIE)

The *E. coli* 3526 (SsIE) antigen was included in the published genome sequence for *E. coli* strain IHE3034 as gene ECOK1_3385 (GenBank accession number CP001969; SEQ ID NO: 15 herein). The sequences of 3526 (SsIE) antigen from many strains have been published since then. Various immunogenic fragments of the antigen have also been reported. Preferred 3526 (SsIE) antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 15; and/or (b) comprising a fragment of at least 'n' consecutive amino acids of SEQ ID NO: 15, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 15. The most useful 3526 (SsIE) antigens of the invention can elicit antibodies which, after administration to a subject, can bind to a polypeptide consisting of amino acid sequence SEQ ID NO: 15. Advantageous 3526 (SsIE) antigens for use with the invention can elicit functional antibodies after administration to a subject.

E. coli 405 (FdeC)

The E. coli 405 (FdeC) antigen was included in the published genome sequence for E. coli strain IHE3034 as gene ECOK1_0290 (GenBank accession number CP001969;). The sequences of 405 (FdeC) antigen from many strains have been published since then. Various immunogenic fragments of the antigen have also been reported. Preferred 405 (FdeC) antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) of the sequences of 405 (FdeC) antigen, more preferably as indicated in the herein Seq ID No. 16; and/or (b) comprising a fragment of at least 'n' consecutive amino acids of 405 (FdeC) antigen, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 16. The most useful 405 (FdeC) antigens of the invention can elicit antibodies which, after administration to a subject, can bind to 405 antigen. Advantageous 405 (FdeC) antigens for use with the invention can elicit functional antibodies after administration to a subject.

NHBA Antigen.

The NHBA antigen was included in the published genome sequence for meningococcal serogroup B strain MC58 as gene NMB2132 (GenBank accession number GI:7227388; SEQ ID NO: 2 herein). The sequences of NHBA antigen from many strains have been published since then. Various immunogenic fragments of the NHBA antigen have also been reported. Preferred NHBA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 2; and/or (b) comprising a fragment of at least 'n' consecutive amino acids of SEQ ID NO: 2, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 2. The most useful NHBA antigens of the invention can elicit antibodies which, after administration to a subject, can bind to a meningococcal polypeptide consisting of amino acid sequence SEQ ID NO: 2. Advantageous NHBA antigens for use with the invention can elicit bactericidal anti-meningococcal antibodies after administration to a subject.

NadA Antigen.

The NadA antigen was included in the published genome sequence for meningococcal serogroup B strain MC58 (see e.g. Tettelin et al. (2000) Science 287:1809-1815) as gene NMB1994 (GenBank accession number GI:7227256; SEQ ID NO: 3 herein). The sequences of NadA antigen from many strains have been published since then, and the protein's activity as a Neisserial adhesin has been well documented. Various immunogenic fragments of NadA have also been reported. Preferred NadA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 3; and/or (b) comprising a fragment of at least 'n' consecutive amino acids of SEQ ID NO: 3, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 3. The most preferred NadA antigens of the invention can elicit antibodies which, after administration to a subject, can bind to a meningococcal polypeptide consisting of amino acid sequence SEQ ID NO: 3. Advantageous NadA antigens for use with the invention can elicit bactericidal anti-meningococcal antibodies after administration to a subject. SEQ ID NO: 7 is one such fragment.

NspA Antigen.

The NspA antigen was included in the published genome sequence for meningococcal serogroup B strain MC58 (see e.g. Tettelin et al. (2000) Science 287:1809-1815) as gene NMB0663 (GenBank accession number GI:7225888; SEQ ID NO: 4 herein). The sequences of NspA antigen from many strains have been published since then. Various immunogenic fragments of NspA have also been reported. Preferred NspA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 4; and/or (b) comprising a fragment of at least 'n' consecutive amino acids of SEQ ID NO: 4, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 4. The most preferred NspA antigens of the invention can elicit antibodies which, after administration to a subject, can bind to a meningococcal polypeptide consisting of amino acid sequence SEQ ID NO: 4. Advantageous NspA antigens for use with the invention can elicit bactericidal anti-meningococcal antibodies after administration to a subject.

NhhA Antigen.

The NhhA antigen was included in the published genome sequence for meningococcal serogroup B strain MC58 (see e.g. Tettelin et al. (2000) Science 287:1809-1815) as gene NMB0992 (GenBank accession number GI:7226232; SEQ ID NO: 5 herein). The sequences of NhhA antigen from many strains have been published since e.g. WO00/66741 and WO01/55182, and various immunogenic fragments of NhhA have been reported. It is also known as Hsf. Preferred NhhA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 5; and/or (b) comprising a fragment of at least 'n' consecutive amino acids of SEQ ID NO: 5, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 5. The most preferred NhhA antigens of the invention can elicit antibodies which, after administration to a subject, can bind to a meningococcal polypeptide consisting of amino acid sequence SEQ ID NO: 5. Advantageous NhhA antigens for use with the invention can elicit bactericidal anti-meningococcal antibodies after administration to a subject.

App antigen.

The App antigen was included in the published genome sequence for meningococcal serogroup B strain MC58 (see e.g. Tettelin et al. (2000) Science 287:1809-1815) as gene NMB1985 (GenBank accession number GI:7227246; SEQ ID NO: 6 herein). The sequences of App antigen from many strains have been published since then. Various immunogenic fragments of App have also been reported. Preferred App antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 6; and/or (b) comprising a fragment of at least 'n' consecutive amino acids of SEQ ID NO: 6, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 6. The most preferred App antigens of the invention can elicit antibodies which, after administration to a subject, can bind to a meningococcal polypeptide consisting of amino acid sequence SEQ ID NO: 6. Advantageous App antigens for use with the invention can elicit bactericidal anti-meningococcal antibodies after administration to a subject.

fHbp Antigen.

The factor H binding protein exists as three variants (v1, v2 and v3), and the invention can use any of these as preferred embodiment.

A v1 fHbp preferably comprises (a) an amino acid sequence which has at least k'% identity to SEQ ID NO: 8, and/or (b) a fragment of SEQ ID NO: 8. k' refers to percentage identity and could be defined as any number from 1 to 100. With reference to amino acid or nucleic acid sequences, generally the identity used in the application starts from as low as 40% with specific references to higher percentages, i.e. 70%, 75%, 80%, etc.

The fragment will preferably include at least one epitope from SEQ ID NO: 8. Preferably, the v1 fHbp can elicit antibodies which are bactericidal against v1 strains e.g. against strain MC58 (available from the ATCC as 'BAA-335').

A v2 fHbp preferably comprises (a) an amino acid sequence which has at least k'% identity to SEQ ID NO: 1, and/or (b) a fragment of SEQ ID NO: 1. Information about 'k' and fragments are given above. The fragment will preferably include at least one epitope from SEQ ID NO: 1. Preferably, the v2 fHbp can elicit antibodies which are bactericidal against v2 strains e.g. against strain M2091 (ATCC 13091).

A v3 fHbp preferably comprise (a) an amino acid sequence which has at least k'% identity to SEQ ID NO: 9, and/or (b) a fragment of SEQ ID NO: 9. Information about 'k' and fragments are given above. The fragment will preferably include at least one epitope from SEQ ID NO: 9. Preferably, the v3 fHbp can elicit antibodies which are bactericidal against v3 strains e.g. against strain M01-240355.

Antigens from Group A *Streptococcus* (GAS), Group B *Streptococcus* (GBS) and Pneumococcus are also equally preferred. As non-limiting examples, GAS25 (Slo), GAS40 (SpyAD) and GAS57 (SpyCEP) antigens can be incorporated into conjugates in accordance with some embodiments of the invention.

*Plasmodium* antigens are further preferred. These can be from any suitable species, where preferred species are selected from: *P. falciparum, P. vivax* and *P. ovale*.

Still another preferred antigen is Pfs25 (SEQ ID NO: 10), which is a sexual stage antigen of *P. falciparum* expressed on the surface of zygote and ookinete forms of the parasite. Another preferred antigen is Pfs48/45, which is a transmission-blocking vaccine candidate. Recently the C-terminal 10 cysteine fragment (10C) of Pfs48/45, containing three known epitopes for transmission blocking antibodies, has been produced as a chimera with the N-terminal portion of GLURP (RO), the asexual blood-stage antigen glutamate-rich protein. The resulting fusion protein (R010C) elicited high levels of transmission-blocking antibodies in rodents (see Theisen et al. (2014) Vaccine 32:2623-2630). Shing et al. (2015) Vaccine 33:1981-1986 describes a chimera containing truncated 6C-fragments, which increases the yield of correctly-folded conformer. The RO6C construct was able to elicit high titer transmission blocking antibodies in rats.

RO6C (SEQ ID NO: 11) is a preferred antigen that can be conjugated according to the present invention.

Another preferred antigen is the circumsporozoite protein (CSP; SEQ ID NO: 12).

Shorter peptides from CSP may also be conjugated according to the present invention. For example, the 12 amino acid (NANP) 3 peptide (SEQ ID NO: 13) derived from CSP can be used according to preferred embodiments.

In another still preferred embodiment the antigens are a saccharide species. The invention is in fact also suitable for conjugating one or more selected saccharide antigens to nOMVs, whereby saccharides may be used in their full-length natural form. As an alternative, a particular size fraction can also advantageously be selected. Thus, a saccharide may be fragmented from their natural length, and optionally a size fraction of these fragments can be used. Even further, the saccharides are not limited to saccharides purified from natural sources and synthetic or semi-synthetic saccharides can be used instead.

Preferred saccharide antigens are bacterial capsular saccharides (CPSs). These include, but are not limited to, the capsular saccharides selected from at least one of: *Haemophilus influenzae* type B and type A; *Neisseria meningitidis* serogroups A, C, W135, X and Y; *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F; *Salmonella* including *Salmonella enterica* serovar *Typhi* Vi, either full length or fragmented (indicated as fVi); *Shigella* sp, group A and B *Streptococcus* (GAS and GBS respectively).

In any case, and as above mentioned, the selected antigens could be conjugated to nOMVs derived from the same or even from a different bacterial strain, thus providing a multivalent vaccine. In this respect, in a more preferred embodiment of the invention, the nOMV and the saccharide antigen are derived from different bacterial strains.

Other preferred saccharide antigens are 8-glucans, particularly useful for protecting against *C. albicans* (for a general reference see Sandlin et al. (1995) Infect. Immun., 63:229-37).

Other preferred saccharide antigens are poly-rhamnose oligosaccharides for protecting against Group A *Streptococcus* (GAS). Native GAS saccharide has a poly-rhamnose backbone substituted with NAcGlcN. Synthetic oligosaccharides of poly-rhamnose, or oligomers with the structure of native GAS saccharide, can be conjugated to nOMVs according to the invention.

As formerly set forth, in a further aspect, the invention refers to a process for preparing the present conjugates, comprising the steps of:

i) activating at least a nOMV saccharide moiety, generally bond to the nOMV surface;

ii) connecting the thus obtained activated saccharide to at least one selected antigen to obtain an antigen-nOMV intermediate;

iii) reacting at least a surface protein residue of the antigen-nMOV intermediate of the step ii) with the first terminal portion of a bivalent Linker to obtain an antigen-nOMV-Linker intermediate; and iv) connecting said nOMV-Linker intermediate to at least one different antigen via the second terminal portion of the bivalent Linker, thus obtaining an antigen-nOMV-Linker-antigen conjugate of the invention.

According to the present process, the nOMV-surface bond saccharides are first activated by oxidation, and then reacted with the selected antigens, more preferably under reductive amination conditions. Subsequently, the thus functionalized nOMV is reacted with the linker and then connected through this latter to a different antigen.

As preferred embodiment, nOMV vesicles, preferably GMMA, from MenB are first functionalized with saccharide from MenC through linkage to saccharide moiety on the nOMV surface via reductive amination. Then, the thus obtained nOMV-MenC vesicles are conjugated to the MenA saccharide via BS3 linker targeting a protein moiety on nOMV, providing the final MenC, MenA nOMV conjugate.

As still preferred embodiment, nOMV vesicles, preferably GMMA, from MenB are first functionalized with antigen from MenA through linkage to saccharide moiety on the nOMV surface via reductive amination. Then, the thus obtained nOMV-MenA vesicles are conjugated to the MenC antigen via BS3 linker targeting a protein moiety on nOMV, providing the final MenA, MenC nOMV conjugate.

As preferred embodiment, nOMV vesicles, preferably GMMA, from S. sonnei are first functionalized with the antigen 405 through linkage to saccharide moiety on the nOMV surface via reductive amination. Then, the thus obtained nOMV-405 vesicles are conjugated to the 3526 antigen via BS3 linker targeting a protein moiety on nOMV, providing the final 405, 3526 nOMV conjugate.

As still preferred embodiment, nOMV vesicles, preferably GMMA, from S. sonnei are first functionalized with antigen from 3526 through linkage to saccharide moiety on the nOMV surface via reductive amination. Then, the thus obtained nOMV-3526 vesicles are conjugated to the 405 antigen via BS3 linker targeting a protein moiety on nOMV, providing the final 3526, 405 nOMV conjugate.

The two functionalization procedures (through saccharide and through a surface protein-linker as per steps i-ii and iii-iv respectively) can be performed in any order. This means that in a still preferred embodiment of the invention, the nOMV can be first conjugated to an antigen via a protein and linker connection, and subsequently conjugated to a different antigen via a surface saccharide moiety.

Thus, the present invention refers to a process comprising the steps of:
  i) reacting at least a nMOV surface protein residue with the first terminal portion of a bivalent Linker to obtain a nOMV-Linker intermediate, and
  ii) connecting said nOMV-Linker intermediate to at least one selected foreign antigen via the second terminal portion of the bivalent Linker, thus obtaining the nOMV-Linker-antigen intermediate;
  iii) activating at least a nOMV saccharide moiety of the nOMV-Linker-antigen intermediate of step ii), and
  iv) connecting the thus obtained activated saccharide to at least a different antigen, thus obtaining the antigen-nOMV-Linker-antigen conjugates of the invention.

Figure 3:
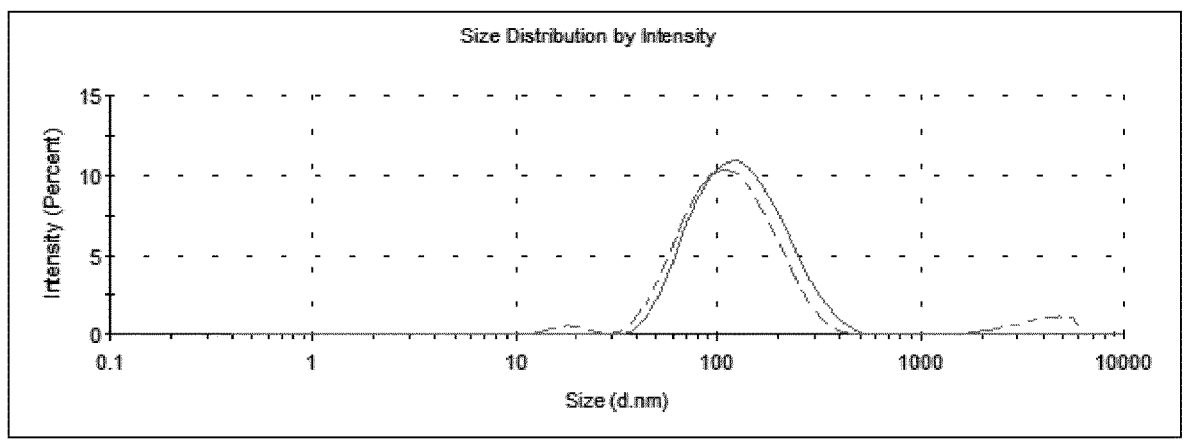
FIG. 3: DLS analysis of the nOMV conjugate (dotted line) obtained by first conjugation of GMMA from *S. sonnei*, with *E. coli* 405 via BS3, and subsequently conjugated to *E. coli* 3526 via polysaccharide oxidation and reductive amination with NaBH$_3$CN, compared to starting GMMA (continue line) and showing no GMMA aggregation after conjugation.

According to one embodiment, the present invention refers to a process for the preparation of conjugates obtained by connecting nOMV, preferably GMMA from S. sonnei, with E. coli 405 and E. coli 356. To that, said nOMV, preferably GMMA from S. sonnei, are first connected to the E. coli 405 antigen through BS3 linker to give nOMV-B53-E. coli 405 derivative. This latter is thus subjected to oxidation and reaction with the E. coli 3526 and NaBH$_3$CN, thus connecting the antigen to the nOMV vesicle through reductive amination and leading to the obtainment of the bi-functionalized nOMV conjugate in a selective and reproducible way. Of note, DLS analysis showed a size distribution of the thus obtained nOMV confirming that no aggregation occurs, as indicated in FIG. 3.

Advantageously, the process of the invention can be repeated to further conjugate the nOMV to additional different antigens, thus providing a new and reliable way to obtain multivalent immunogenic nOMV, useful for the preparation of corresponding immunogenic compositions and vaccines.

According to the present process, at least one saccharide moiety on a nOMV is conjugated to one selected antigen to form a conjugate of the invention. As above indicated, the conjugation typically involves activating the nOMV-surface saccharide moiety and/or the selected antigen. Thus, in one embodiment, the process of the invention comprises the steps of: (i) activating a saccharide moiety on the nOMV surface by oxidation; and (ii) direct connection of the activated moiety with a selected antigen.

The conjugation can also involve introducing a linker between the nOMV-saccharide moiety and the selected antigen, as below detailed. Thus, as an alternative embodiment, the process of the invention comprises the steps of: (i) activating a saccharide moiety on the nOMV surface by oxidation; (ii) connecting said activated saccharide moiety to a bivalent linker to form a nOMV-linker intermediate; and (iii) connecting a selected antigen to said nOMV-linker intermediate, to form a nOMV-Linker-antigen conjugate.

As another alternative embodiment, the process of the invention comprises the steps of: (i) activating a saccharide moiety on the nOMV surface; (ii) connecting a selected antigen to a bivalent linker to form an antigen-linker derivative; and (iii) connecting the activated moiety of step (i) to said antigen-linker derivative to form a nOMV-Linker-antigen conjugate.

As another alternative embodiment, the process of the invention comprises the steps of: (i) activating a saccharide moiety on the nOMV surface; (ii) connecting said activated moiety to a bivalent linker to form a nOMV-linker intermediate; (iii) connecting a selected antigen to a bivalent linker group to form an antigen-linker derivative; and (iv) connecting the nOMV-linker intermediate of step (ii) to the antigen-linker derivative of step (iii) to form a nOMV-Linker-antigen conjugate of the invention.

As far as the nOMV saccharide moiety is concerned, it has to be noted that it can be part of the —OAg functionality, or of the core region naturally present on the surface of the nOMV (e.g. in LPS or LOS), or it can be present within a different nOMV surface portions, e.g. a CPS. In all these preferred cases, the process of the invention allows the connection of said saccharide moiety with a selected antigen in a simple and effective way, thus leading to final nOMV-antigen conjugates endowed with remarkable immunogenic activity. Depending on the species from which nOMVs are prepared, various saccharide moieties (including tetraose, pentose and hexose sugars) can be used for activation and subsequent conjugation. Preferably, lipopolysaccharides, via the —OAg portion or core region, or capsular saccharides may be used for activation and subsequent conjugation. Preferred saccharide moieties are selected from at least one of: glucose, galactose, fructose, mannose, ribose, abequose, galactosamine, glucosamine, mannosamine, sialic acid, sulfoquinovose, erythrose, threose, arabinose, rhamnose, sorbose, ribulose, xylose, xylulose, lyxose, tagatose or keto-deoxyoctulosonate.

A saccharide moiety on the nOMV is preferably activated by oxidizing a hydroxyl group of the saccharide to form a carbonyl aldehyde functionality, in the presence of an oxidizing agent.

Preferred oxidizing agent are TEMPO or a periodated salt. This latter is preferably selected from an alkali periodate or a metaperiodate, more preferably NaIO$_4$. The oxidizing agent is preferably used as aqueous solution in a concentration ranging from 0.5 mM to 20 mM, preferably from 3 mM to 20 mM, where concentrations from 10 to 20 mM and from 0.5 to 5 mM or from 3 to 5 mM are still more preferred. Other activation reactions according to some embodiments occurs in the presence of: cyanylating reagents such as CDAP (e.g. 1-cyano-4-dimethylamino pyridinium tetrafluoroborate), carbodiimides, hydrazides, active esters, norborane, p-nitrobenzoic acid, N-hydroxysuccinimide, S—NHS, EDC and TSTU.

In general, where polysaccharides are oxidised it is not necessary to oxidise all of the available sugars. Indeed, it can be desirable to retain at least part of the natural sugar structures, particularly where these are a useful antigen. Also to be noted is the fact that due to the peculiar nOMVs composition and conformation as above detailed, the polysaccharide moiety can be conveniently activated by the present process leading to the formation of a highly reactive oxidized nOMVs intermediate species. In a preferred embodiment, for a given saccharide moiety of interest, the proportion of oxidised residues can range from 1% to 100%, preferably from 10-50%, or from 20-40%, or from 20-35%, whereas oxidation of 20-35% within an —OAg structure is particularly preferred. In this direction, it has been found that said ranges allow for efficient conjugation with minor or substantially assent impact on the —OAg structural integrity. Also, it has been noticed that higher nOMV oxidation degree corresponds to lower —OAg size, meaning that there is major impact on native —OAg structure and its ability to induce a specific immune response. The proportion of oxidised residues can be determined by high-performance anion exchange chromatography with pulsed amperometric detection (HPAEC-PAD), by comparing the intact sugar residues pre- and post-oxidation. In this direction, it was found that the concentration of the oxidising agent and of the nOMV, along with the pH may influence the overall conduct of the oxidation step. Thus, in a preferred embodiment, the oxidation agent is used in excess over the starting nOMV, where a molar excess of 3:1 or 2:1 respect to the number of monosaccharides that can be subjected to oxidation is particularly preferred. The oxidizing agent is preferably used as aqueous solution in a concentration ranging from 0.5 mM to 20 mM, preferably from 3 mM to 20 mM, where concentrations from 10 to 20 mM and from 0.5 to 5 or from 3 to 5 mM are still more preferred.

The concentration of nOMV is preferably comprised between 0.2 and 5 mg/mL.

Preferably, the pH is comprised between 4 and 8, whereas value from 5 and 7 are particularly preferred. To this extent, the pH may be adjusted using a buffer agent, such as acetate/phospate and the like.

Said parameters can be conveniently set in order to have a preferred degree of oxidation comprised between 20% and 35% over the subjected saccharide moiety. This allows having an efficient further conjugation with the selected antigen, without substantially impacting the saccharide moiety structure.

For instance, Rha residues in an —OAg functionality can be oxidised as e.g. indicated in the below Scheme 2 using $NaIO_4$.

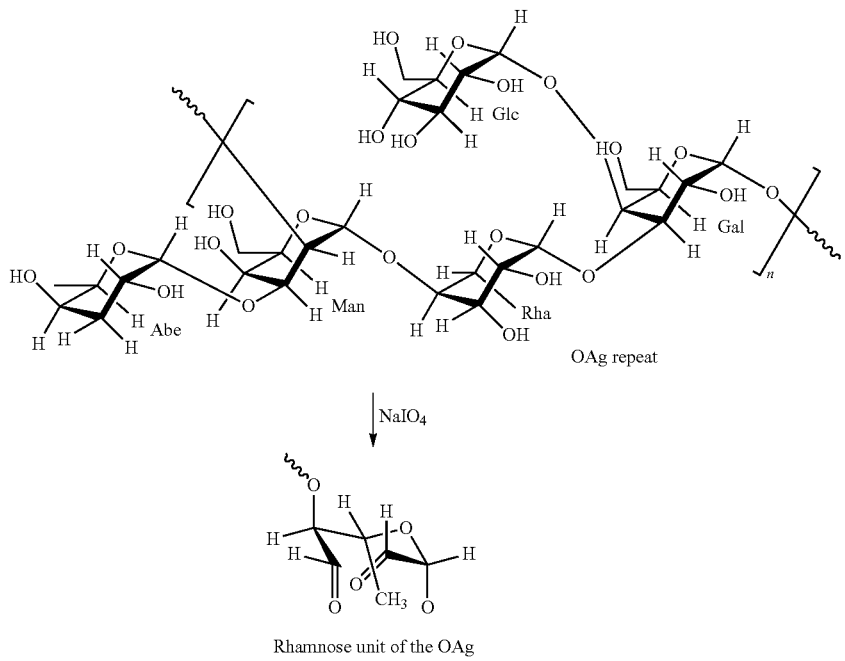

Scheme 2

OAg repeat

Rhamnose unit of the OAg

The oxidation step is typically performed at room temperature (e.g. from about 15° C. to about 40° C.), for a suitable time, e.g. comprised from 30 min to 3 h, depending for example on the amount and type of considered nOMV. In any case, it has been found that no substantial nOMV crosslink and/or aggregation occurred. This is of upmost importance also for the effectiveness of the subsequent conjugation step with the selected antigen as herein described in details.

After oxidation, nOMVs can optionally be subjected to a reduction step, for example with $NaBH_4$, to stabilise the oxidised nOMV by removing the formed CHO groups. The stabilised oxidised nOMV may then be stored and/or further characterised.

Typically, after the activation step of the present process, the obtained oxidized nOMVs are isolated and purified e.g. by ultracentrifugation at 4° C. at 110000 rpm for 30 min, and subsequently reacted with the selected antigen.

Thus in a preferred embodiment, the process comprises the steps of:
(i) activation of the saccharide moiety on the nOMV surface, preferably by oxidation; (i-bis) isolation of the thus obtained oxidised nOMV; and
(ii) connection of the oxidised nOMV of step (i) or (i-bis) with at least a selected antigen, optionally via a bivalent linker, to obtain a antigen-nOMV intermediate,
(iii) reacting at least a surface protein of the antigen-nOMV intermediate of step (ii) with the first terminal portion of a bivalent Linker, to obtain a antigen-nOMV-Linker intermediate, and
(iv) connecting said antigen-nOMV-Linker intermediate to at least one different antigen via the second terminal portion of the bivalent Linker, thus obtaining an antigen-nOMV-Linker-antigen conjugate of the invention.

In a still preferred embodiment, the process is performed in the presence of an alkaline sulphite, preferably $Na_2SO_3$. This is particularly advantageous because by quenching the oxidation reaction with $Na_2SO_3$, it is possible to perform the process in one step, i.e. avoiding the isolation of the intermediate oxidised nOMV (step (i-bis) above). This allows saving time, thus obtaining the final conjugates in a simple and effective way. In practice, and according to an exemplified embodiment, after the activation step (i) the reaction is quenched with a proper amount of the alkaline sulphite, and let to react for a proper frame of time (generally comprised from 5 to 20 minutes) in order to neutralize the excess of the oxidizing agent. After that, the selected antigen is directly added to the mixture (i.e. without isolation of the oxidised nOMV), according to step (ii), followed by steps (iii) and (iv) as above indicated, thus obtaining the final nOMV conjugates of the invention.

As an alternative, the carbonyl aldehyde group of the saccharide moiety obtained by the oxidation step can be further modified to form a proper functionality which can then be reacted with the selected antigen or with a linker as the case may be (in this case to give a vesicle-linker conjugate which can then be coupled to the selected antigen).

The selected antigen is typically added at 1:1 w/w ratio with respect to the used nOMV, at room temperature, for a proper frame of time, e.g. comprised from 2 hours to 24 hours. When the antigen is derivatised with a linker, the reaction is conveniently carried out using an excess of antigen over the nOMV, preferably a 2:1 or more preferably a 3:1 w/w ratio. In a particularly preferred embodiment, the process of the invention comprises the steps of: (i) oxidation of a nOMV saccharide moiety as above set forth; and (ii) connection of the thus obtained oxidized nOMV saccharide moiety to an amino group of a selected antigen residue. Even more preferably, said selected antigen residue is an amino $-NH_2$ group on a lysine residue within a polypeptide selected antigen.

Preferably, connection of the oxidized saccharide moiety of the nOMV with the amino group, preferably a free $-NH_2$ group, of an antigen is achieved by reductive amination, more preferably using $NaBH_3CN$, e.g. according to procedure known in the art. The $NaBH_3CN$ is used in weight amounts (w/w) comprised from 3 to ⅓, preferably 1 to 1, over the oxidized nOMV. Practically, the $NaBH_3CN$ can be added together with the selected antigen, directly to the oxidised nOMV intermediate product, as generally illustrated in Schemes 3 and 4 below, using, by way of example, a nOMV that is conjugated via an oxidized rhamnose unit to malaria membrane proteins Pfs25 or RO6C, respectively.

Scheme 3

Scheme 4

As an alternative embodiment, the selected antigen may be modified, either by introducing a linker group or by converting a functional group on the antigen into another functional group suitable for the reaction with the activated saccharide moiety on the nOMV, or with a linker of the nOMV-linker conjugate when used. In particular, if the selected antigen is a saccharide, it may be modified by reaction with a linker either randomly (r), meaning that the linker is introduced at multiple points along the sugar chain, or selectively (s), meaning that the linker is introduced at the reducing end of the sugar chain (i.e. at only one position). In a preferred embodiment, the linker is selective introduced at the terminal position of the selected antigen.

Selective modification of the antigen is preferably achieved by reaction with adipic acid dihydrazide (ADH) in the presence of $NaBH_3CN$, as generally shown in Scheme 5 using fVi as the antigen. Random modification of the antigen is preferably achieved by activation of one or more carboxylic acid groups on the antigen, for instance by using NHS/EDAC, and subsequent reaction with ADH, as shown in Scheme 6 using fVi as the antigen. This type of conjugation reaction is illustrated in Scheme 7 below, using, by way of example, a nOMV that is conjugated via an oxidized rhamnose unit to fVi modified to include a —NH$_2$ by reaction with ADH.

Scheme 5

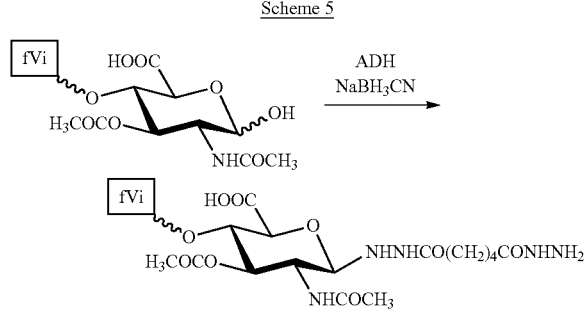

Scheme 6

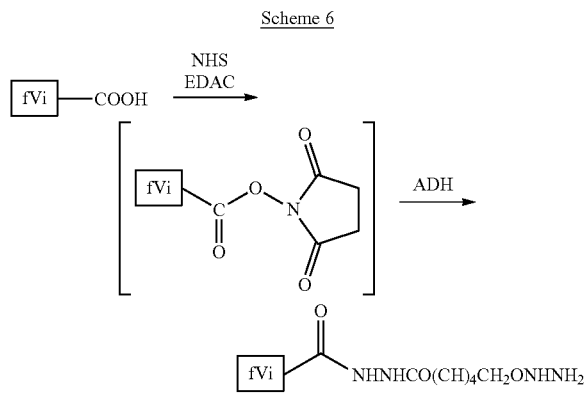

Scheme 7

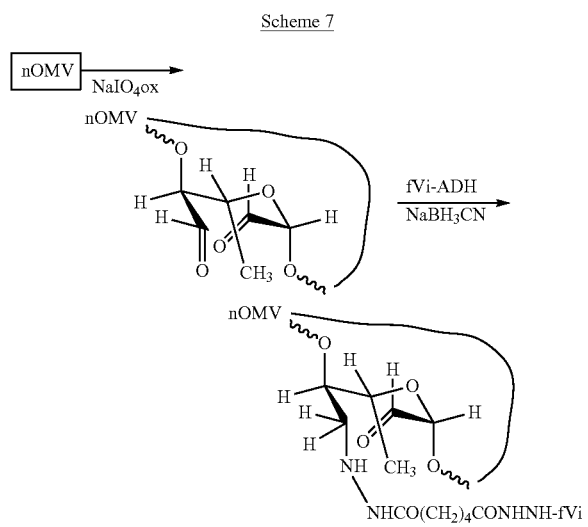

As above set forth in details, the nOMV-antigen conjugates of the invention comprise an activated nOMV surface saccharide moiety directly connected to a selected antigen.

In an equally preferred embodiment, the activated nOMV surface saccharide moiety is connected to the selected antigen indirectly, e.g. via a linker unit. This latter will generally be a bifunctional linker, using one functional group to react with the nOMV (via the activated saccharide moiety) and another functional group to react with the selected antigen. The linker can be a heterobifunctional linker or a homobifunctional linker of general formula (I):

wherein:
X and X' groups are independently the same or different as each other, and react with activated nOMV surface saccharide moiety and the selected antigen respectively; and
L is a linking spacer, preferably of general formula (II):

wherein:
the two L' groups are independently the same or different as each other and are selected from: a carbonyl (C=O), ester (—C(O)O—) or amido group (—C(O)NR1-), wherein R1 is H or, a straight, or, when comprising at least 3 carbon atoms, a branched cyclic C1-C10 alkyl group having 1 to 10 carbon atoms (e.g. C1, C2, C3, C4, C5, C6, C7, C8, C9, C10); and
L2 is a straight or branched C1-C10 alkyl group having 1 to 10 carbon atoms, preferably having C4 carbon atom, even more preferably in the form of a straight chain.
X group is preferably selected from: —NH$_2$, —NH—NH$_2$, —O—NH$_2$, optionally substituted sulfo-N-hydroxysuccinimide and N oxysuccinimide residue.

Where the reactions with both the nOMV and the selected antigen involve the same functional groups it is preferred to use a bifunctional linker of general formula (I), wherein both the two X groups are the same.

When the functional groups on the nOMV saccharide moiety and on the selected antigen are both aldehydes it is preferred to use a homofunctional linker having X selected from: —NH$_2$, —NH—NH$_2$ or —O—NH$_2$ reactive group. In a still preferred embodiment, the linker is the adipic acid dihydrazide (ADH) of general formula:

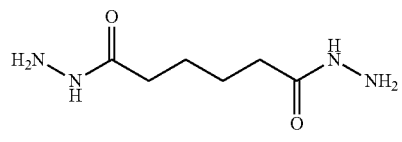

ADH

The linker may then be reacted with the nOMV and/or antigen by reductive amination as above set forth.

Preferred bifunctional linkers particularly useful for the reaction with amine groups of the selected antigen, are selected from: acryloyl halides, preferably chloride, disuccinimidyl glutarate, disuccinimidyl suberate and ethylene glycol bis[succinimidylsuccinate].

Other still preferred linkers are selected from: β-propionamido, nitrophenyl-ethylamine, haloacyl halides, glycosidic derivatives linkages, 6-aminocaproic acid.

In a still preferred embodiment, the linker is selected from: N-hydroxysuccinimide, N oxysuccinimide, even more preferably from adipic acid N-hydroxysuccinimide diester (SIDEA).

When the reaction with the nOMV and the antigen involves different functional groups (such as an amine on the nOMV and a thiol on the antigen,) it will be understood that a heterobifunctional linker will be used capable to selectively react with both the different functional groups. In this case, preferred heterobifunctional linkers are selected from at least one of: succinimidyl 3-(2-pyridyldithio)propionate (SPDP), succinimidyl 6-(3[2-pyridyldithio]-propionamido)hexanoate (LC-SPDP), sulfosuccinimidyl 6-(3'-(2-pyridyldithio)propionamido)hexanoate (sulfo-LC-SPDP), 4-succinimidyloxycarbonyl-α-methyl-α-(2-pyridyldithio)toluene (SMPT), sulfosuccinimidyl-6-[α-methyl-α-(2-pyridyldithio)tolueamideo]hexanoate (sulfo-LC-SMPT), succinimidyl 4-(N-maleimidomethyl)cyclohexane-1-carboxylate (SMCC), sulfosuccinimidyl 4-(N-maleimidomethyl)cyclohexane-1-carboxylate (suflo-SMCC), m-maleimidobenzoyl-N-hydroxysuccinimide ester (MBS), m-maleimidobenzoyl-N-hydroxysulfosuccinimide ester (sulfo-MBS), N-succinimidyl (4-iodoacetyl)aminobenzoate (STAB), sulfosuccinimidyl (4-iodoacetyl)aminobenzoate (sulfo-SIAB), succinimidyl 4-(N-maleimidophenyl)butyrate (SMPB), sulfosuccinimidyl 4-(N-maleimidophenyl)butyrate (sulfo-SMPB), N-γ-maleimidobutyryl-oxysuccinimide ester (GMBS), N-γ-maleimidobutyryl-oxysulfosuccinimide ester (sulfo-GMBS), succinimidyl-6-((((4-(iodoacetyl)amino)methyl)cyclohexane-1-carbonyl)amino)hexanoate (SIACX), succinimidyl 6[6-(((iodoacetyl)amino)hexanoyl)amino]hexanoate (SIAXX), succinimidyl-4-(((iodoacetyl)amino)methyl)cyclohexane-1-carboxylate (SIAC), and succinimidyl 6-[(iodoacetyl)amino]hexanoate (SIAX) and p-nitrophenyl iodoacetate (NPIA).

In a further embodiment, the process encompasses the possibility to recycle the unreacted selected antigen particularly when in form of polypeptide. To this extent, it has been found that the unreacted antigen from the conjugation mixture can be conveniently recycled in the conjugation step, thus improving the overall efficiency of production of the derivatives of the invention.

As above set forth, the invention refers to a process for preparing multi-functionalized nOMV-antigen conjugates, comprising the reaction of at least a nOMV protein residue with a first terminal portion of a bivalent Linker, according to the above indicated formula (I) X-L-X', followed by reaction of the second terminal portion of such bivalent Linker with one or more selected foreign antigens, as herein below described in more details. Of note, this selective functionalization can be performed before or after the functionalization of the same nOMV with a different antigen via a polysaccharide residue, according to the above described embodiment.

Where the reactions with the protein on the surface of the vesicle and the antigen involve different functional groups (such as an amine on the protein on the vesicle and a thiol on the antigen, or vice versa) it is preferred to use a heterobifunctional Linker of the above general formula (I) X-L-X', where X and X' are different to each other and as above defined and L is a moiety as above defined. The X group can react with one functional group, e.g. an amine on the nOMV protein; whereas X' group can react with a different functional group, e.g. a thiol on the selected antigen. Preferably, the X group is N-hydroxysuccinimide or N-oxysuccinimide or derivatives thereof, whereas the X' group is selected from at least one of: 2-pyridyldithio, maleimide or iodoacetyl group.

The percentage of nOMV-Linker functionalization is comprised from 15% to 60%, mainly depending on the kind of bivalent linker used. To this regard, the % of reactive functional groups at the free terminal end of the Liker is comprised from 15% to 40%, preferably from 30% to 35%, depending on the kind and stability of said reactive functional groups. It is in fact noticed that such ranges allow for an implemented efficacy of the process, thus resulting in higher amount of final antigen conjugate derivative of the invention.

The thus obtained buffered suspension has a nOMV concentration comprised from 2 and 10 mg/mL, preferably from 3 to 6 mg/mL. The chosen Linker, is generally added in amounts depending e.g. on the —$NH_2$ groups on the nOMV, preferably in excess, even more preferably comprised from 10 to 20 equivalents per mole of —$NH_2$.

Depending on the Linker, it could be convenient to preventively solve it in a polar dry solvent, such as DMSO or the like, in order to facilitate the handling and the efficacy, thus obtaining improved results in terms of overall yield and reproducibility.

The mixture is then incubated at room temperature (e.g. comprised from about 15 to 40° C.) for a period of time generally comprised from 30 minutes to 4 hours. Subsequently, the thus obtained nOMV-Linker intermediate is purified, e.g. by ultracentrifugation, and then reacted with the selected antigen according to step ii). The antigen is generally solved in a proper buffer solution, such as phosphate buffered saline. The antigen is preferably added in an amount ranging from 2:1 to 1:2 w/w ratio over the intermediated activated nOMV or more preferably in a 1:1 ratio. The reaction is carried out for a proper frame of time, up to the formation of the final nOMV-Linker-antigen derivative according to the invention. The reaction can be monitored e.g. by HPLC/SEC and the final product formation can be confirmed by SDS page/western blot analysis.

The skilled person will understand that when a homobifunctional Linker is used, the protein and the antigen functional groups involved in the reaction will be the same chemical entity, as above explained in details.

Thus, according to one preferred embodiment, the process of the present invention comprises the steps of:

(i) reaction of a —$NH_2$ group of at least a nOMV protein surface with a bivalent homobifunctional Linker to form a nOMV-Linker intermediate, wherein the nOMV has been previously functionalized with a selected antigen, through a saccharide moiety as above set forth; and (ii) connection of said intermediate with a —$NH_2$ group of one or more selected different antigen(s) to form a conjugate of the invention.

An alternative conjugation process of the invention includes reacting the antigen with a first Linker and a protein on the vesicle with a second Linker, then reacting the first and second Linker together to form the conjugate.

By way of example, either the antigen or the protein on the OMV may be reacted with a Linker terminating in a maleimide group, for instance by reacting a primary amine or either the antigen or the protein on the nOMV with succinimidyl-4-(N-maleimidomethyl)cyclohexane-1-carboxylate (SMCC) or N-(γ-maleimidobutyryloxy)succinimide ester (GMBS). A thiol on either the antigen or the protein on the nOMV may then be reacted with the maleimide. The thiol may be native to the protein on the nOMV or antigen or the thiol may be the result of reacting the protein on the nOMV or antigen with a separate Linker. This type of conjugation reaction is exemplified in Scheme 8 below, using, by way of example, GMMA and fHbp as the antigen:

Scheme 8

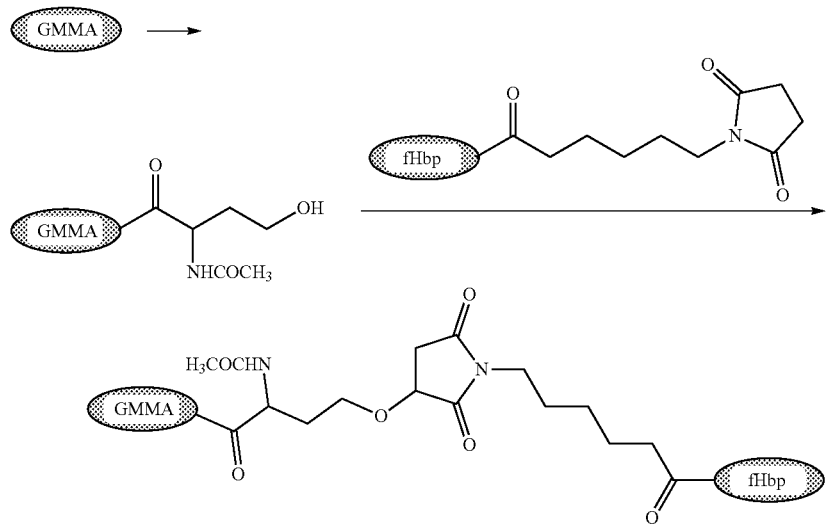

Advantageously, due to its versatility, the invention can be used for the preparation of a variety of conjugates, particularly appreciated by the skilled person when faced with the problem to find convenient and reliable methodologies for obtaining immunogenic derivatives.

As a further alternative, a protein on the nOMV may be linked to the antigen by (i) modifying the nOMV protein to include an alkyne; (ii) modifying the antigen to include an azide, then (iii) reacting the alkyne and azide, known as "click chemistry". Alternatively, the antigen may be modified to include an alkyne and the vesicle may be modified to include an azide. This type of conjugation reaction is illustrated in Scheme 9 below, using, by way of example, GMMA as the vesicle and fHbp as the antigen and using copper free click chemistry.

Scheme 9

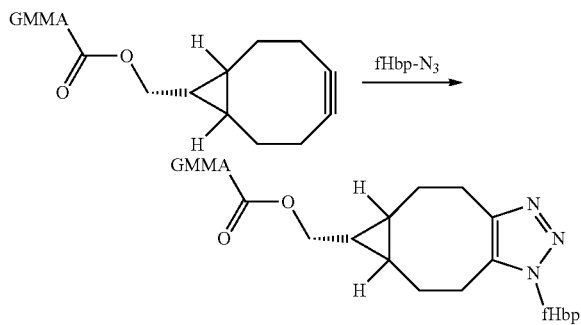

According to a further aspect, the invention refers to the above described nOMV conjugates for use as medicament, particularly as immunogenic agents, even more preferably for one or more of the pathogens as herein indicated. In other words, the invention refers to the use of the present nOMV conjugates for the manufacture of an immunogenic composition, preferably a vaccine.

As above explained in details, the present process allows the preparation of the desired immunogenic nOMV conjugates in a simple and convenient way, also requiring fewer steps when compared to previous methods for the preparation of similar conjugates(e.g. starting from dOMV). Thus the invention also refers to a nOMV conjugates obtained (or obtainable) by the process of the invention, according to the above described embodiments. Particularly, the present process does not necessarily require the expensive step of polypeptide antigen derivatisation, as well as not performing an extraction (e.g. using a detergent) or denaturation of the starting vesicles. Production and purification of nOMVs of the invention in fact is less expensive than for traditional carrier proteins and more robust and consistent than production of dOMV. nOMV used in the invention can be produced at high yields using e.g. two simple tangential flow filtration steps, and avoiding detergent extraction procedures. Also, the present invention offers an easy way to prepare a polyvalent immunogenic composition, e.g. a vaccine which includes multiple immunogens (typically from different pathogens) by properly choosing the nOMV and the selected antigens as herein described in more details. In fact, due to its versatility, the present process may be conveniently and effectively applied to nOMV from different sources (e.g. *Salmonella, Shigella* and meningococcal), being applied with success to both protein and saccharide antigens, according to the presently described selective conjugations. Finally, it has to be noted that the present process not only allows for the preparation of highly immunogenic derivatives, but also it does not substantially change the nOMV integrity and size distribution. This is particularly appreciated by the skilled in the art, because the absence of nOMV aggregates allows for a better yield and overall consistency and robustness of the present process.

Conjugates of the invention which include nOMVs from one pathogen and at least two different antigens from a second pathogen can be useful as immunogenic composition, preferably as multivalent vaccines. Pairs of pathogens which may be combined (one as antigen, and the other as a nOMV vesicle) include, but are not limited to: *N. meningitidis* and non-typhoidal *Salmonella* (e.g. *Salmonella Typhimurium* or *Salmonella Enteritidis*); *P. falciparum* and non-typhoidal *Salmonella*; *Salmonella Typhi* and non-typhoidal *Salmonella*; *E. coli* and *Shigella* sp.; Group A *Streptococcus*

(GAS) and *N. meningitidis*; and GAS and non-typhoidal *Salmonella*, Hib and *N. meningitidis*, Hib and Pertussis.

Preferred nOMV-polysaccharide-antigen combinations of the invention are indicated in the following Table 1.

TABLE 1 preferred nOMV-Antigen conjugates obtained by oxidation of nOMV polysaccharide residues

| nOMV | Antigen |
|---|---|
| *Salmonella Typhimurium* | *Neisseria meningitidis* fHbp |
| *Salmonella Typhimurium* | *Plasmodium falciparum* CSP |
| *Salmonella Typhimurium* | *Plasmodium falciparum* Pfs25 |
| *Salmonella Typhimurium* | *Plasmodium falciparum* RO6C |
| *Salmonella Typhimurium* | *Plasmodium falciparum* RO10C |
| *Salmonella Typhimurium* | *Escherichia coli* CTF1232 |
| *Salmonella Typhimurium* | *S.* Typhi Vi saccharide |
| *Neisseria meningitidis* | *Neisseria meningitidis* fHbp |
| *Neisseria meningitidis* | *Neisseria meningitidis* NHBA |
| *Neisseria meningitidis* | Poly-rhamnose oligosaccharide |
| *Shigella* | *Escherichia coli* CTF1232 |
| *Shigella* | *Escherichia coli* FdeC |
| *Shigella* | *Escherichia coli* SsIE |
| *Salmonella Typhimurium* | Synthetic or native GAS PS |
| *Neisseria meningitidis* | Synthetic or native GAS PS |
| *Salmonella Typhimurium* | Synthetic or native GBS PS |
| *Neisseria meningitidis*, preferably B | *Neisseria meningitidis* ser A saccharide |
| *Neisseria meningitidis*, preferably B | *Neisseria meningitidis* ser C saccharide |
| *Salmonella Typhimurium* | *Neisseria meningitidis* ser A saccharide |
| *Salmonella Typhimurium* | *Neisseria meningitidis* ser C saccharide |
| *B. pertussis* | *Haemophilus influenzae* type b |
| *Neisseria meningitidis*, preferably B | *Haemophilus influenzae* type b |
| *B. pertussis* | *Haemophilus influenzae* type a |
| *Neisseria meningitidis*, preferably B | *Haemophilus influenzae* type a |
| *Salmonella Typhimurium* | *Streptococcus pneumoniae* saccharide |
| *Neisseria meningitidis* | *Streptococcus pneumoniae* saccharide |

Preferred nOMV-Linker-antigen conjugates of the invention are indicated in the following Table 2.

preferred nOMV-Linker-Antigen conjugates obtained by connection of a nOMV surface to a selected antigen via a Linker
Table 2

| nOW | Linker | Antigen |
|---|---|---|
| *Salmonella Typhimurium* | BS3 | *Plasmodium falciparum* Pfs25 |
| *Salmonella Typhimurium* | BS(PEG)₅ | *Plasmodium falciparum* Pfs25 |
| *Salmonella Typhimurium* | BS3 | fHbp (*Neisseria meningitidis*) |
| *Salmonella Typhimurium* | BS(PEG)₅ | fHbp (*Neisseria meningitidis*) |
| *Salmonella Typhimurium* | BS3 | *Plasmodium falciparum* RO6C |
| *Salmonella Typhimurium* | BS(PEG)₅ | *Plasmodium falciparum* RO6C |
| *Salmonella Typhimurium* | BS3 | *Plasmodium falciparum* CSP |
| *Salmonella Typhimurium* | BS(PEG)₅ | *Plasmodium falciparum* CSP |
| Meningococcal B | BS3 | fHbp (*Neisseria meningitidis*) |
| Meningococcal B | BS(PEG)₅ | fHbp (*Neisseria meningitidis*) |
| Meningococcal B | BS3 | NHBA (*Neisseria meningitidis*) |
| Meningococcal B | BS(PEG)₅ | NHBA (*Neisseria meningitidis*) |
| *Salmonella Typhimurium* | BS3 | Synthetic or native GAS PS |
| *Salmonella Typhimurium* | BS(PEG)₅ | Synthetic or native GAS PS |
| *Salmonella Typhimurium* | BS3 | Synthetic or native GBS PS |
| Meningococcal B | BS3 | Synthetic or native GAS PS |
| Meningococcal B | BS3 | Hib PS |
| *B. pertussis* | BS3 | Hib PS |
| Meningococcal B | BS3 | Hia PS |
| *B. pertussis* | BS3 | Hia PS |
| *Salmonella Typhimurium* | BS3 | Vi PS |
| *Shigella* | BS3 | *E. coli* FdeC |
| *Shigella* | BS3 | *E. coli* SsIE |
| *Shigella* | BS3 | *E. coli* CTF1232 |
| Meningococcal B | BS3 or SIDEA | *Neisseria meningitidis* ser C saccharide |
| Meningococcal B | BS3 or SIDEA | *Neisseria meningitidis* ser A saccharide |
| *Salmonella Typhimurium* | BS3 or SIDEA | *Neisseria meningitidis* ser C saccharide |
| *Salmonella Typhimurium* | BS3 or SIDEA | *Neisseria meningitidis* ser A saccharide |
| *Salmonella Typhimurium* | BS3 or SIDEA | *Streptococcus pneumoniae* saccharide |
| *Neisseria meningitidis* | BS3 or SIDEA | *Streptococcus pneumoniae* saccharide |

Thus, the present nOMV-antigen derivatives are particularly useful as immunogenic agents against the pathogens listed in Table 1 and 2.

Of note, any combination of the antigen listed in Table 1 and in Table 2 is encompassed by the present invention as preferred embodiments.

Still further preferred multi-functionalization patterns of the nOMV according to the present invention are indicated in Table 3:

| nOMV | Antigen 1 (via PS) | Antigen2/linker |
|---|---|---|
| *Salmonella Typhimurium* | Pfs25 | (NANP)₃ |
| Meningococcal B | MenA | MenC/SIDEA or BS3 |
| Meningococcal B | MenC | MenA/SIDEA or BS3 |
| *Salmonella Typhimurium* | MenA | MenC/SIDEA or BS3 |
| *Salmonella Typhimurium* | MenC | MenA/SIDEA or BS3 |
| *Salmonella Typhimurium* | Native or synthetic GAS PS | *Neisseria meningitidis* fHbp/BS3 |
| *Salmonella Typhimurium* | *Neisseria meningitidis* fHbp | Native or synthetic GAS PS/BS3 |
| Meningococcal B | Hia PS | Hib PS/SIDEA or BS3 |
| *B. Pertussis* | Hia PS | Hib PS/SIDEA or BS3 |
| *Salmonella Typhimurium* | Hia PS | Hib PS/SIDEA or BS3 |
| Meningococcal B | Hib PS | Hia PS/SIDEA or BS3 |
| *B. Pertussis* | Hib PS | Hia PS/SIDEA or BS3 |
| *Salmonella Typhimurium* | Hib PS | Hia PS/SIDEA or BS3 |
| *Shigella* | SsIE | FdeC/BS3 |
| *Shigella* | FdeC | SsIE/BS3 |

Thus, the present nOMV-antigen derivatives are particularly useful as immunogenic agents against the pathogens listed in Tables 1, 2 and 3.

In table 1, 2 and 3, the listed nOMVs are preferably GMMA.

In a further embodiment the invention provides a composition comprising a conjugate of the invention and at least two antigens selected from the following:
- a saccharide antigen from *N. meningitidis* serogroup A, C, W135 and/or Y,
- a saccharide antigen from *Streptococcus pneumonia*,
- an antigen from hepatitis A virus, such as inactivated virus,
- an antigen from hepatitis B virus, such as the surface and/or core antigens,
- a diphtheria antigen, such as a diphtheria toxoid e.g. the CRM197 mutant,
- a tetanus antigen, such as a tetanus toxoid,
- an antigen from *Bordetella pertussis*, such as pertussis holotoxin (PT) and filamentous haemagglutinin (FHA) from *B. pertussis*, optionally also in combination with pertactin and/or agglutinogens 2 and 3,
- a saccharide antigen from *Haemophilus influenzae* A or B,
- polio antigen(s) such as IPV,
- measles, mumps and/or rubella antigens, influenza antigen(s), such as the haemagglutinin and/or neuraminidase surface proteins,
- an antigen from *Moraxella catarrhalis*,
- an protein antigen from *Streptococcus agalactiae* (group B *streptococcus*),
- a saccharide antigen from *Streptococcus agalactiae* (group B *streptococcus*),
- an antigen from *Streptococcus pyogenes* (group A *streptococcus*),
- an antigen from *Staphylococcus aureus*.

Advantageously in this respect, the thus functionalized GMMA vesicle can be used for the preparation of trivalent vaccine against *Meningitidis* Serogroups B, C and A. Since the different nature of the three serogroups, the present combination is particularly valuable since it can provide a valid multivalent immunogenic composition, usable against these different kinds of pathogens.

According to a further aspect, the invention refers to the above described nOMV-antigen conjugates for use as a medicament, particularly as immunogenic agent, even more preferably for one or more of the pathogens as herein indicated. In other words, the invention refers to the use of the present nOMV-antigen conjugated derivative for the manufacture of an immunogenic composition.

According to a further aspect, the invention thus refers to an immunogenic composition, preferably a vaccine, comprising a conjugate of the invention and at least one additional pharmaceutically acceptable carrier, excipient or adjuvant. Generally, pharmaceutically acceptable carrier or excipient, can be any substance that does not itself induce the production of antibodies harmful to the patient receiving the composition, and which can be administered without undue toxicity. Pharmaceutically acceptable carriers and excipient are those used in the art, and can include liquids such as water, saline, glycerol and ethanol. Auxiliary substances, such as wetting or emulsifying agents, pH buffering substances, and the like, can also be present in such vehicles, according to the prior art.

The invention also provides a method for raising an immune response in a vertebrate, preferably a mammal, comprising administering a conjugate of the invention to the mammal or other vertebrate. The invention also provides conjugates of the invention for use in such methods. The immune response is preferably protective and preferably involves antibodies. The method may raise a booster response.

The mammal is preferably a human. The subject in which disease is prevented may not be the same as the subject that receives the conjugate of the invention. For instance, a conjugate may be administered to a female (before or during pregnancy) in order to protect offspring (so-called 'maternal immunisation'). Conjugates of the invention may also be used to immunize other mammals e.g. cattle, sheep and pigs (especially against *Salmonella* sp.), and other non-mammal vertebrates including fish and poultry.

The invention provides conjugates of the invention for use in therapy (e.g. as immunogenic compositions or as vaccines). The invention also provides a conjugate of the invention for use in a method for raising an immune response in a vertebrate, preferably a mammal. The invention also provides the use of a conjugate of the invention in the manufacture of a medicament for raising an immune response in a vertebrate, preferably a mammal. The uses and methods are particularly useful for preventing/treating a variety of diseases, depending on the antigens and nOMVs within the conjugates as above set forth. Preferred conjugates of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Immunogenic compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration is preferred e.g. to the thigh or the upper arm. Injection may be via a needle (e.g. a hypodermic needle), but needle-free injection may alternatively be used. A typical intramuscular dose is about 0.5 ml. The invention may also be used to elicit systemic and/or mucosal immunity. Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

Infections affect various areas of the body and so the compositions of the invention may be prepared in various forms. For example, the compositions may be prepared as injectable, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared for nasal, aural or ocular administration e.g. as drops. Compositions suitable for parenteral injection are most preferred. The composition is preferably sterile. It is preferably pyrogen-free. It is preferably buffered e.g. at between pH 6 and pH 8, generally around pH 7. Compositions of the invention may be isotonic with respect to humans. Immunogenic compositions comprise an immunologically effective amount of a conjugate of the invention, as well as any other of other specified components, as needed. Dosage treatment may be a single dose schedule or a multiple dose schedule (e.g. including booster doses). The composition may be administered in conjunction with other immunoregulatory agents.

Adjuvants which may be used in compositions of the invention include, but are not limited to insoluble metal salts, oil-in-water emulsions (e.g. MF59 or AS03, both containing squalene), saponins, non-toxic derivatives of LPS (such as monophosphoryl lipid A or 3-O-deacylated MPL), immunostimulatory oligonucleotides, detoxified bacterial ADP-ribosylating toxins, microparticles, liposomes, imidazoquinolones, or mixtures thereof. Other substances that act as immunostimulating agents are disclosed for instance in Watson, Pediatr. Infect. Dis. J. (2000) 19:331-332. The use of an aluminium hydroxide and/or aluminium phosphate adjuvant is particularly preferred. These salts include oxyhydroxides and hydroxyphosphates. The salts can take any suitable form (e.g. gel, crystalline, amorphous, etc.).

The invention will be now described by the following experiment part, without posing any limitation to its scope.

EXPERIMENTAL PART

Example 1: nOMV Production

Preferred nOMV vesicles were prepared from ΔtolR strains of S. Typhimurium or S. sonnei, as e.g. disclosed in Clin Vaccine Immunol. 2016 April; 23(4): 304-314 and PLoS One. 2015; 10(8): e0134478 respectively.

Characteristics of the purified nOMV vesicles were as indicated in the following Table 1:

TABLE 1 characteristics of nOMV vesicles prepared from ΔtolR strains of S. Typhimurium or S. sonnei.

|  | S. Typhimurium 1418 (☐tolhR) | S. sonnei 1790 (☐tolR ☐htrB) |
|---|---|---|
| Diameter (nm) | 131.5 | 140 |
| Surface charge (mV) | −14.1 | −9.87 |
| Lipid A/mg vesicles | 172.8 | 155.4 |
| OAg/total protein weight ratio | 0.84 | 0.039 |

Figure 2:
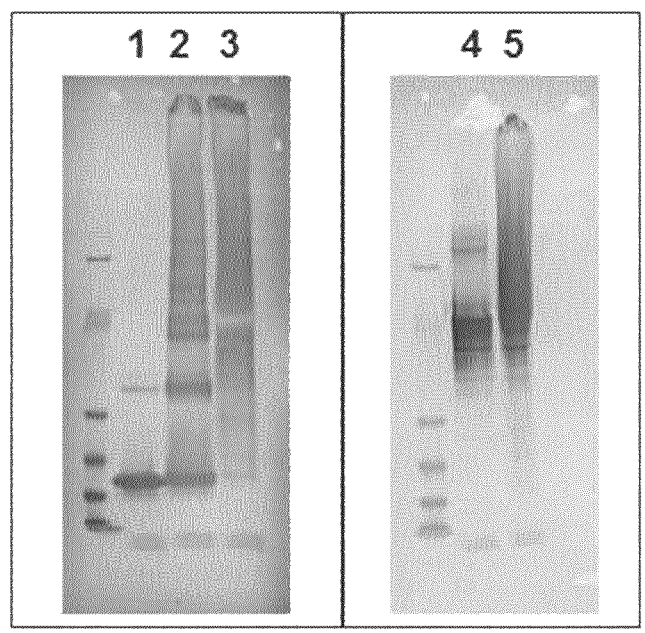
FIG. 2 shows western blot analysis of a GMMA vesicle functionalized with *E. coli* 405 and *E. coli* 3526 according to the present invention, and as schematically represented in FIG. 1.

Example 2: Functionalization of GMMA from S. sonnei with E. coli 405 (FdeC) Via BS3 Chemistry and with E. coli 3526 (SsIE) Via Reductive Amination GMMA from S. sonnei have been activated with BS3 linker, under the following conditions:
pH: 9 (100 mM borate buffer);
BS3 concentration: 50 mg/mL;
GMMA concentration: 4 mg/mL;
30 min reaction time at 25° C.;
Purification by UC (110000 rpm, 16 min, 4° C.).
Resulting GMMA had 43.8% of $NH_2$ groups derivatised with the BS3 linker according to TNBS colorimetric method. Purified activated GMMA were added of 405 protein antigen in PBS buffer with a w/w ratio of GMMA to 405 of 1:1 and a GMMA concentration of 6.45 mg/mL. After overnight gently mixing at room temperature, the conjugate (S. sonnei GMMA BS3-405) was purified by ultracentrifuge (110000 rpm, 4° C. 1h) and resuspended in NaPi 100 mM pH 6.5 for further conjugation step. The conjugate was characterised by SDS PAGE/western blot, confirming conjugate formation (FIG. 2). S. sonnei GMMA BS3-405 conjugate at the concentration of 2.1 mg/mL was incubated with $NaIO_4$ 5 mM for 30 minutes at 25° C., in the dark. Excess of $NaIO_4$ was quenched with $Na_2SO_3$ at a final concentration of 10 mM, for 15 minutes at room temperature. 3526 protein antigen (w/w ratio of GMMA conjugate to 3526 1:1 and with GMMA concentration of 1.18 mg/mL) and $NaBH_3CN$ (few mg) were directly added to the reaction mixture. After overnight gently mixing at room temperature, the conjugate (S. sonnei GMMA BS3-405)ox-3526) was purified by ultracentrifuge (110000 rpm 4° C. 1h), re-suspended in PBS and analysed by SDS PAGE/western blot, that confirmed both presence of 405 and 3526 antigens on GMMA particles (FIG. 2).

Example 3a-c: Comparative Examples

Example 3a: Reaction of dOMV (from Neisseria meningitidis B) with fHbp v3 (No Reaction)

The dOMVs of the present example have been prepared by a detergent extraction process, where the deoxhycholate is used as selected detergent. The thus obtained detergent extracted vesicles have been reacted with the selected antigen (fHbp) according to process of the present invention. In particular, dOMV, at the concentration of 0.96 mg/mL, were incubated with $NaIO_4$ 10 mM for 30 minutes at room temperature, in the dark. Excess of $NaIO_4$ was quenched with $Na_2SO_3$ at a final concentration of 20 mM, for 15 minutes at room temperature. fHbp (w/w ratio of dOMV to fHbp 1:1 and with dOMV concentration of 0.335 mg/mL) and $NaBH_3CN$ (3 mg) were directly added to the reaction mixture. After overnight gently mixing at room temperature, the crude was purified by ultracentrifuge (110000 rpm 4° C. 1h) and re-suspended in PBS. Analysis by SDS PAGE/western blot showed no dOMV-fHbp conjugate formation.

Example 3b: Reaction of nOMV (from Neisseria meningitidis B) with fHbp v3 (Formation of the nOMV-fHbp Intermediate)

The nOMVs of the present example have been prepared without using any detergent, as described in Koeberling et al. Vaccine (2014) 32:2688. The thus obtained extracted vesicles have been reacted with the selected antigen (fHbp) according to the process of the present invention. In particular, nOMV at the concentration of 0.96 mg/mL were incubated with $NaIO_4$ 5 mM for 30 minutes at room temperature, in the dark. Excess of $NaIO_4$ was quenched with $Na_2SO_3$ at a final concentration of 20 mM, for 15 minutes at room temperature. fHbp (w/w ratio of dOMV to fHbp 1:1 and with dOMV concentration of 0.335 mg/mL) and $NaBH_3CN$ (3 mg) were directly added to the reaction mixture. After overnight gently mixing at room temperature, the conjugate was purified by ultracentrifuge (110000 rpm 4° C. 1h), re-suspended in PBS and analysed by SDS PAGE/western blot, confirming the formation of the desired nOMV-fHbp conjugate.

Example 3c: Reaction of nOMV (from *Salmonella*) with fHbp v1, Following the Procedure of Example 3b The same experiment as Examples 3b has been performed using nOMV from *Salmonella Typhimurium*, and similar results have been collected, obtaining the nOMV-fHbp conjugate of the invention.

Example 4 (Comparative): dOMV Conjugation Via BS3 Linker dOMV (from MenB) has been tested as starting material for reaction with BS3 linker, under the following conditions:
pH: 6.5;
BS3 concentration: 50 mg/mL;
dOMV concentration: 1.011 mg/mL;
30 min reaction time at 25° C.;
Purification by UC (110 Krpm, 16 min, 4° C.).

The reaction provides dOMV aggregates and side products as major results. Aggregation/crosslinking has been verified by dls analysis and SEC/MALS.

The comparative example shows that independently from the order by which the process for multiple functionalization is intended (i.e. first connecting the vesicle to an antigen via saccharide residue, followed by subsequent connection to a second antigen via protein, or vice versa), when dOMVs are considered as vesicles of choice, no functionalization is possible since even at very early stages, the reaction only provides aggregate derivatives as main product.

```
                      SEQUENCE LISTING

>SEQ ID NO: 1 [fHbp v2]
VAADIGAGLADALTAPLDHKDKSLQSLTLDQSVRKNEKLKLAAQGAEKTYGNGDSLNTGKLKN
DKVSRFDFIRQIEVDGQLITLESGEFQIYKQDHSAVVALQIEKINNPDKIDSLINQRSFRVSGLGG
EHTAFNQLPDGKAEYHGKAFSSDDAGGKLTYTIDFAAKQGHGKIEHLKTPEQNVELAAAELKA
DEKSHAVILGDTRYGSEEKGTYHLALFGDRAQEIAGSATVKIGEKVHEIGIAGKQ

>SEQ ID NO: 2 [NHBA]
MFKRSVIAMACIFALSACGGGGGGSPDVKSADTLSKPAAPVVSEKETEAKEDAPQAGSQGQG
APSAQGSQDMAAVSEENTGNGGAVTADNPKNEDEVAQNDMPQNAAGTDSSTPNHTPDPNM
LAGNMENQATDAGESSQPANQPDMANAADGMQGDDPSAGGQNAGNTAAQGANQAGNNQA
AGSSDPIPASNPAPANGGSNFGRVDLANGVLIDGPSQNITLTHCKGDSCSGNNFLDEEVQLKS
EFEKLSDADKISNYKKDGKNDKFVGLVADSVQMKGINQYIIFYKPKPTSFARFRRSARSRRSLP
AEMPLIPVNQADTLIVDGEAVSLTGHSGNIFAPEGNYRYLTYGAEKLPGGSYALRVQGEPAKGE
MLAGAAVYNGEVLHFHTENGRPYPTRGRFAAKVDFGSKSVDGIIDSGDDLHMGTQKFKAAIDG
NGFKGTWTENGSGDVSGKFYGPAGEEVAGKYSYRPTDAEKGGFGVFAGKKEQD

>SEQ ID NO: 3 [NadA]
MKHFPSKVLTTAILATFCSGALAATSDDDVKKAATVAIVAAYNNGQEINGFKAGETIYDIGEDGTI
TQKDATAADVEADDFKGLGLKKVVTNLTKTVNENKQNVDAKVKAAESEIEKLTTKLADTDAALA
DTDAALDETTNALNKLGENITTFAEETKTNIVKIDEKLEAVADTVDKHAEAFNDIADSLDETNTKA
DEAVKTANEAKQTAEETKQNVDAKVKAAETAAGKAEAAAGTANTAADKAEAVAAKVTDIKADIA
TNKADIAKNSARIDSLDKNVANLRKETRQGLAEQAALSGLFQPYNVGRFNVTAAVGGYKSESA
VAIGTGFRFTENFAAKAGVAVGTSSGSSAAYHVGVNYEW

>SEQ ID NO: 4 [NspA]
MKKALATLIALALPAAALAEGASGFYVQADAAHAKASSSLGSAKGFSPRISAGYRINDLRFAVDY
TRYKNYKAPSTDFKLYSIGASAIYDFDTQSPVKPYLGARLSLNRASVDLGGSDSFSQTSIGLGVL
TGVSYAVTPNVDLDAGYRYNYIGKVNTVKNVRSGELSAGVRVKF

>SEQ ID NO: 5 [NhhA]
MNKIYRIIWNSALNAWVVVSELTRNHTKRASATVKTAVLATLLFATVQASANNEEQEEDLYLDP
VQRTVAVLIVNSDKEGTGEKEKVEENSDWAVYFNEKGVLTAREITLKAGDNLKIKQNGTNFTYS
LKKDLTDLTSVGTEKLSFSANGNKVNITSDTKGLNFAKETAGTNGDTTVHLNGIGSTLTDTLLNT
GATTNVTNDNVTDDEKKRAASVKDVLNAGWNIKGVKPGTTASDNVDFVRTYDTVEFLSADTKT
TTVNVESKDNGKKTEVKIGAKTSVIKEKDGKLVTGKDKGENGSSTDEGEGLVTAKEVIDAVNKA
GWRMKTTTANGQTGQADKFETVTSGTNVTFASGKGTTATVSKDDQGNITVMYDVNVGDALNV
NQLQNSGWNLDSKAVAGSSGKVISGNVSPSKGKMDETVNINAGNNIEITRNGKNIDIATSMTPQ
FSSVSLGAGADAPTLSVDGDALNVGSKKDNKPVRITNVAPGVKEGDVTNVAQLKGVAQNLNN
RIDNVDGNARAGIAQAIATAGLVQAYLPGKSMMAIGGGTYRGEAGYAIGYSSISDGGNWIIKGT
ASGNSRGHFGASASVGYQW

>SEQ ID NO: 6 [App]
MKTTDKRTTETHRKAPKTGRIRFSPAYLAICLSFGILPQAWAGHTYFGINYQYYRDFAENKGKF
AVGAKDIEVYNKKGELVGKSMTKAPMIDFSVVSRNGVAALVGDQYIVSVAHNGGYNNVDFGAE
GRNPDQHRFTYKIVKRNNYKAGTKGHPYGGDYHMPRLHKFVTDAEPVEMTSYMDGRKYIDQN
NYPDRVRIGAGRQYWRSDEDEPNNRESSYHIASAYSWLVGGNTFAQNGSGGGTVNLGSEKIK
HSPYGFLPTGGSFGDSGSPMFIYDAQKQKWLINGVLQTGNPYIGKSNGFQLVRKDWFYDEIFA
GDTHSVFYEPRQNGKYSFNDDNNGTGKINAKHEHNSLPNRLKTRTVQLFNVSLSETAREPVYH
AAGGVNSYRPRLNNGENISFIDEGKGELILTSNINQGAGGLYFQGDFTVSPENNETWQGAGVHI
SEDSTVTWKVNGVANDRLSKIGKGTLHVQAKGENQGSISVGDGTVILDQQADDKGKKQAFSEI
GLVSGRGTVQLNADNQFNPDKLYFGFRGGRLDLNGHSLSFHRIQNTDEGAMIVNHNQDKEST
VTITGNKDIATTGNNNSLDSKKEIAYNGWFGEKDTTKTNGRLNLVYQPAAEDRTLLLSGGTNLN
GNITQTNGKLFFSGRPTPHAYNHLNDHWSQKEGIPRGEIVWDNDWINRTFKAENFQIKGGQAV
VSRNVAKVKGDWHLSNHAQAVFGVAPHQSHTICTRSDWTGLTNCVEKTITDDKVIASLTKTDIS
GNVDLADHAHLNLTGLATLNGNLSANGDTRYTVSHNATQNGNLSLVGNAQATFNQATLNGNT
SASGNASFNLSDHAVQNGSLTLSGNAKANVSHSALNGNVSLADKAVFHFESSRFTGQISGGKD
TALHLKDSEWTLPSGTELGNLNLDNATITLNSAYRHDAAGAQTGSATDAPRRRSRRSRRSLLS
VTPPTSVESRFNTLTVNGKLNGQGTFRFMSELFGYRSDKLKLAESSEGTYTLAVNNTGNEPAS
```

SEQUENCE LISTING

```
LEQLTVVEGKDNKPLSENLNFTLQNEHVDAGAWRYQLIRKDGEFRLHNPVKEQELSDKLGKAE
AKKQAEKDNAQSLDALIAAGRDAVEKTESVAEPARQAGGENVGIMQAEEEKKRVQADKDTALA
KQREAETRPATTAFPRARRARRDLPQLQPQPQPQPQRDLISRYANSGLSEFSATLNSVFAVQD
ELDRVFAEDRRNAVWTSGIRDTKHYRSQDFRAYRQQTDLRQIGMQKNLGSGRVGILFSHNRT
ENTFDDGIGNSARLAHGAVFGQYGIDRFYIGISAGAGFSSGSLSDGIGGKIRRRVLHYGIQARYR
AGFGGFGIEPHIGATRYFVQKADYRYENVNIATPGLAFNRYRAGIKADYSFKPAQHISITPYLSLS
YTDAASGKVRTRVNTAVLAQDFGKTRSAEWGVNAEIKGFTLSLHAAAAKGPQLEAQHSAGIKL
GYRW

>SEQ ID NO: 7 [NadA fragment]
ATNDDDVKKAATVAIAAAYNNGQEINGFKAGETIYDIDEDGTITKKDATAADVEADDFKGLGLKK
VVTNLTKTVNENKQNVDAKVKAAESEIEKLTTKLADTDAALADTDAALDATTNALNKLGENITTF
AEETKTNIVKIDEKLEAVADTVDKHAEAFNDIADSLDETNTKADEAVKTANEAKQTAEETKQNVD
AKVKAAETAAGKAEAAAGTANTAADKAEAVAAKVTDIKADIATNKDNIAKKANSADVYTREESD
SKFVRIDGLNATTEKLDTRLASAEKSIADHDTRLNGLDKTVSDLRKETRQGLAEQAALSGLFQP
YNVG >SEQ ID NO: 8 [fHbp v1]
VAADIGAGL ADALTAPLDH KDKGLQSLTL DQSVRKNEKL KLAAQGAEKT YGNGDSLNTG
KLKNDKVSRF DFIRQIEVDG QLITLESGEF QVYKQSHSAL TAFQTEQIQD SEHSGKMVAK
RQFRIGDIAG EHTSFDKLPE GGRATYRGTA FGSDDAGGKL TYTIDFAAKQ GNGKIEHLKS
PELNVDLAAA DIKPDGKRHA VISGSVLYNQ AEKGSYSLGI FGGKAQEVAG SAEVKTVNGI
RHIGLAAKQ >SEQ ID NO: 9 [fHbp v3]
VAADIGTGLADALTAPLDHKDKGLKSLTLEDSIPQNGTLTLSAQGAEKTFKAGDKDNSLNTGKL
KNDKISRFDFVQKIEVDGQTITLASGEFQIYKQNHSAVVALQIEKINNPDKTDSLINQRSFLVSGL
GGEHTAFNQLPGGKAEYHGKAFSSDDPNGRLHYSIDFTKKQGYGRIEHLKTLEQNVELAAAEL
KADEKSHAVILGDTRYGSEEKGTYHLALFGDRAQEIAGSATVKIGEKVHEIGIAGKQ >SEQ ID NO: 10 [Pfs25]
KVTVDTVCKR GFLIQMSGHL ECKCENDLVL VNEETCEEKV LKCDEKTVNK PCGDFSKCIK
IDGNPVSYAC KCNLGYDMVN NVCIPNECKQ VTCGNGKCIL DTSNPVKTGV CSCNIGKVPN
VQDQNKCSKD GETKCSLKCL KEQETCKAVD GIYKCDCKDG FIIDQESSIC T >SEQ ID NO: 11 [R06C]
AERSTSENRNKRIGGPKLRGNVTSNIKFPSDNKGKIIRGSNDKLNKNSEDVLEQSEKSLVSENV
PSGLDIDDIPKESIFIQEDQEGQTHSELNPETSEHSKDLNNNGSKNESSDIISENNKSNKVQNHF
ESLSDLELLENSSQDNLDKDTISTEPFPNQKHKDLQQDLNDEPLEPFPTQIHKDYKEKNLINEED
SEPFPRQKHKKVDNHNEEKNVFHENGSANGNQGSLKLKSFDEHLKDEKIENEPLVHENLSIPN
DPIEQILNQPEQETNIQEQLYNEKQNVEEKQNSQIPSLDLKEPTNEDILPNHNPLENIKQSESEIN
HVQDHALPKENIIDKLDNQKEHIDQSQHNINVLQENNINNHQLEPQEKPNIESFEPKNIDSEIILPE
NVETEEIIDDVPSPKHSNHETFEEETSESEHEEAVSEKNAHETVEHEETVSQESNPEKADNDG
NVSQNSNNELNENEFVESEKSEHEARSKPKYEKKVIHGCNFSSNVSSKHTFTDSLDISLVDDSA
HISCNVHLSEPKYNHLVGLNCPGDIIPDCFFQVYQPESEELEPSNIVYLDSQINIGDIEYYEDAEG
DDKIKLFGIVGSIPKTTSFTCICKKDKKSAYMTVTIDSARSHHHHHH >SEQ ID NO: 12 [CSP]
MLFQEYQCYGSSSNTRVLNELNYDNAGTNLYNELEMNYYGKQENWYSLKKNSRSLGENDDG
NNNNGDNGREGKDEDKRDGNNEDNEKLRKPKHKKLKQPGDGNPDPNANPNVDPNANPNVD
PNANPNVDPNANPNANPNANPNANPNANPNANPNANPNANPNANPNANPNANPNANPNANP
NANPNANPNVDPNANPNANPNANPNANPNANPNANPNANPNANPNANPNANPNANPNANPN
ANPNANPNANPNANPNANPNANPNKNNQGNGQGHNMPNDPNRNVDENANANNAVKN
NNNEEPSDKHIEKYLKKIQNSLSTEWSPCSVTCGNGIQVRIKPGSANKPKDELDYENDIEKKICK
MEKCSSVFNWNSSIGLILEHHHHHH

>SEQ ID NO: 13 [(NANP)3]
NANPNANPNANP

>SEQ ID NO: 14 [CTF1232]
QDQRYISIRNTDTIWLPGNICAYQFRLDNGGNDEGFGPLTITLQLKDKYGQTLVTRKMETEAFG
DSNATRTTDAFLETECVENVATTEIIKATEESNGHRVSLPLSVFDPQDYHPLLITVSGKNVNLEH
HHHHH

>SEQ ID NO: 15 [3526, SslE]
DTPSVDSGSGTLPEVKPDPTPTPEPTPEPTPDPEPTPDPTPDPEPTPEPEPEPVPTKTGYLTLG
GSQRVTGATCNGESSDGFTFTPGNTVSCVVGSTTIATFNTQSEAARSLRAVDKVSFSLEDAQE
LANSENKKTNAISLVTSSDSCPADAEQLCLTFSSWDRARFEKLYKQIDLATDNFSKLVNEEVEN
NAATDKAPSTHTSTVVPVTTEGTKPDLNASFVSANAEQFYQYQPTEIILSEGQLVDSLGNGVAG
VDYYTNSGRGVTDENGKFSFSWGETISFGIDTFELGSVRGNKSTIALTELGDEVRGANIDQLIH
RYSTTGQNNTRVVPDDVRKVFAEYPNVINEIINLSLSNGATLDEGDQNVVLPNEFIEQFKTGQA
KEIDTAICAKTDGCNEARWFSLTTRNVNDGQIQGVINKLWGVDTNYQSVSKFHVFHDSTNFYG
STGNARGQAVVNISNSAFPILMARNDKNYWLAFGEKRAWDKNELAYITEAPSIVQPENVT
RDTATFNLPFISLGQVGEGKLMVIGNPHYNSILRCPNGYSWGGGVNSKGECTLSGDSDDM
KHFMQNVLRYLSNDIWQPNTKSIMTVGTNLENVYFKKAGQVLGNSAPFAFHEDFTGITVK
QLTSYGDLNPEEIPLLILNGFEYVTQWSGDPYAVPLRADTSKPKLTQQDVTDLIAYLNKG
GSVLIMENVMSNLKEESASSFVRLLDAAGLSMALNKSWNNDPQGYPDRVRQRRATGIWV
```

SEQUENCE LISTING

```
YERYPAADGAQPPYTIDPNTGEVTWKYQQDNKPDDKPKLEVASWQEEVEGKQVTRYAFID
EAEYTTEESLEAAKAKIFEKFPGLQECKDSTYHYEINCLERRPGTDVPVTGGMYVPRYTQ
LNLDADTAKAMVQAADLGTNIQRLYQHELYFRTKGSKGERLNSVDLERLYQNMSVWLWND
TKYRYEEGKEDELGFKTFTEFLNCYANDAYAGGTKCSADLKKSLVDNNMIYGDSSKAGM
MNPSYPLNYMEKPLTRLMLGRSWWDLNIKVDVEKYPGSVSAKGESVTENISLYSNPTKWF
AGNMQSTGLWAPAQQDVTIKSSASVPVTVTVALADDLTGREKHEVALNRPPRVTKTYTLE
ANGEVTFKVPYGGLIYIKGDSKDDVSANFTFTGVVKAPFYKDGEWKNDLDSPAPLGELES
ASFVYTTPKKNLEASNFTGGVAEFAKDLDTFASSMNDFYGRNDEDGKHRMFTYKNLTGHK
HRFTNDVQISIGDAHSGYPVMNSSFSTNSTTLPTTPLNDWLIWHEVGHNAAETPLNVPGA
TEVANNVLALYMQDRYLGKMNRVADDITVAPEYLDESNGQAWARGGAGDRLLMYAQLKEW
AEENFDIKQWYPDGELPKFYSDRKGMKGWNLFQLMHRKARGDDVGNSTFGGKNYCAESNG
NAADTLMLCASWVAQADLSEFFKKWNPGASAYQLPGATEMSFQGGVSSSAYSTLASLKLP
KPEKGPETINKVTEHKMSAE

>SEQ ID NO: 16 [405, FdeC]
VADGQQAYTLTLTAVDSEGNPVTGEASRLRLVPQDTNGVTVGAISEIKPGVYSATVSSTR
AGNVVVRAFSEQYQLGTLQQTLKFVAGPLDAAHSSITLNPDKPVVGGTVTAIWTAKDAND
NPVTGLNPDAPSLSGAAAAGSTASGWTDNGDGTWTAQISLGTTAGELDVMPKLNGQDAAA
NAAKVTVVADALSSNQSKVSVAEDHVKAGESTTVTLVAKDAHGNAISGLSLSASLTGTAS
EGATVSSWTEKGDGSYVATLTTGGKTGELRVMPLFNGQPAATEAAQLTVIAGEMSSANST
LVADNKTPTVKTTTELTFTMKDAYGNPVTGLKPDAPVFSGAASTGSERPSAGNWTEKGNG
VYVSTLTLGSAAGQLSVMPRVNGQNAVAQPLVLNVAGDASKAEIRDMTVKVNNQ
```

What is claimed is:

1. An immunogenic conjugate comprising an isolated, intact native outer membrane vesicle (nOMV), having at least a surface saccharide moiety connected to an antigen, and having at least a surface protein residue connected to a different antigen through a bivalent linker;
wherein said bivalent linker has the general formula (I):

X-L-X'  (I)

wherein:
X and X' are different to each other or the same, and are a functional group able to selectively react with the nOMV protein residue on one hand and with the antigen on the other hand;
-L- is a bivalent linear or branched C1-C15 alkyl or alkenyl group optionally substituted, and optionally interrupted by one or more heteroatom selected from: oxygen (—O—), sulfur (—S—), and nitrogen (NH— or optionally substituted —N— group);
wherein X and X' are N-hydroxysuccinimide ester derivatives selected from at least one of:

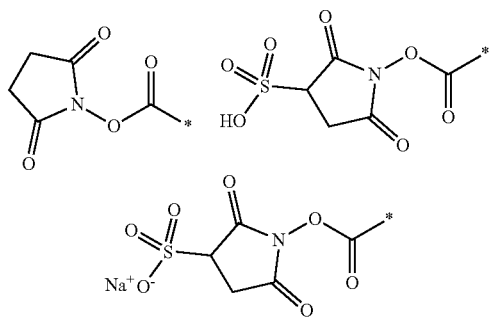

wherein the * represents the point of contact with the -L- group in formula (I);
wherein said nOMV is prepared from *S. sonnei, S. flexneri*, meningococcus, or *Salmonella* bacteria;
wherein said antigen is selected from a group consisting of: *Neisseria meningitidis* fHbp, SsIE, and FdeC;
wherein SsIE comprise an amino acid sequence having 90%, 91%, 92%, 93%, 94%, 95%, 96%, 97%, 98%, 99%, or 99.5% identity to SEQ ID NO: 15;
wherein FdeC comprise an amino acid sequence having 90%, 91%, 92%, 93%, 94%, 95%, 96%, 97%, 98%, 99%, or 99.5% identity to SEQ ID NO: 16; and
wherein *Neisseria meningitidis* fHbp comprise an amino acid sequence comprising SEQ ID NO: 8, SEQ ID NO: 1, or of SEQ ID NO: 9.

2. The conjugate according to claim 1, wherein said bivalent linker is a homobifunctional linker having the formula X=X'.

3. The conjugate according to claim 1, wherein said bivalent linker is BS3 or SIDEA.

4. The conjugate according to claim 1, wherein said nOMV is obtained by a detergent free process, being released into the fermentation broth and purified using a centrifugation and subsequent filtration; or being released into the fermentation broth and purified using two consecutive Tangential Flow Filtration (TFF) steps.

5. The conjugate according to claim 1, wherein the antigens are selected from an immunogenic polypeptide or a capsular polysaccharide.

6. The conjugate according to claim 1, wherein said nOMV and the antigens connected through a surface saccharide moiety and through a bivalent linker respectively are derived from different bacterial strain.

7. The conjugate according to claim 1,
wherein said antigen is selected from a group consisting of: *Neisseria meningitidis* fHbp, *Plasmodium falciparum* CSP, *Plasmodium falciparum* Pfs25, *Plasmodium falciparum* RO6C, *Plasmodium falciparum* RO10C, *Escherichia coli* CTF1232, *S. typhi* Vi saccharide, *Neisseria meningitidis* NHBA, Poly-rhamnose oligosaccharide, *Escherichia coli* FdeC, *Escherichia coli* SslE, Synthetic or native GAS PS, Synthetic or native GBS PS, *Neisseria meningitidis* ser A saccharide, *Neisseria meningitidis* ser C saccharide, *Haemophilus influenzae* type b, *Haemophilus influenzae* type a, and *Streptococcus pneumoniae* saccharide.

8. The conjugate according to claim 1, wherein said bivalent linker is selected from a group consisting of: BS3, BS(PEG)5, and SIDEA.

9. The conjugate according to claim 1,
wherein said antigen/linker is selected from a group consisting of: (NANP)3, MenC/SIDEA or BS3, MenA/SIDEA or BS3, *Neisseria meningitidis* fHbp/BS3, Native or synthetic GAS PS/BS3, Hib PS/SIDEA or BS3, Hia PS/SIDEA or BS3, FdeC/BS3, and SslE/BS3.

10. The conjugate according to claim 1, wherein said nOMV is produced from wild type bacteria or from genetically-modified bacterial strains that are mutated to enhance vesicle production.

11. A process for preparing the conjugate according to claim 1, comprising the steps of:
i) activating at least a nOMV saccharide moiety, generally bond to the nOMV surface, and
ii) connecting the thus obtained activated saccharide to at least one antigen to obtain an antigen-nOMV intermediate;
iii) reacting at least a nOMV surface protein residue of said antigen-nOMV intermediate with the first terminal portion of a bivalent linker, to obtain an antigen-nOMV-linker intermediate, and
iv) connecting the thus obtained antigen-nOMV-linker intermediate to at least a different antigen via the second terminal portion of the bivalent linker, thus obtaining the conjugate;

or i) reacting at least a nOMV surface protein residue with the first terminal portion of a bivalent linker to obtain a nOMV-linker intermediate, and ii) connecting said nOMV-linker intermediate to at least one antigen via the second terminal portion of the bivalent linker, thus obtaining a nOMV-linker-antigen intermediate, iii) activating at least a nOMV saccharide moiety of the thus obtained nOMV-linker-antigen intermediate, and iv) connecting the thus obtained activated saccharide to at least a different antigen, to obtain the conjugate.

12. An immunogenic composition comprising a conjugate according to claim 1 and at least one pharmaceutically acceptable carrier or excipient.

13. A medicament comprising the immunogenic conjugate according to claim 1, and at least one pharmaceutically acceptable carrier or excipient.

14. A method for inducing an immune response in a vertebrate in need thereof, wherein the method comprises administering the medicament according to claim 13 to the vertebrate.

* * * * *